(12) United States Patent
Mao et al.

(10) Patent No.: US 6,844,028 B2
(45) Date of Patent: Jan. 18, 2005

(54) FUNCTIONAL SURFACE COATING

(75) Inventors: Guoqiano Mao, Smyrna, GA (US); Steven W. Metzger, Fort Collins, CO (US); Michael J. Lochhead, Boulder, CO (US)

(73) Assignee: Accelr8 Technology Corporation, Denver, CO (US)

( * ) Notice: Subject to any disclaimer, the term of this patent is extended or adjusted under 35 U.S.C. 154(b) by 0 days.

(21) Appl. No.: 10/180,199

(22) Filed: Jun. 25, 2002

(65) Prior Publication Data

US 2003/0022216 A1 Jan. 30, 2003

Related U.S. Application Data

(60) Provisional application No. 60/301,223, filed on Jun. 26, 2001.

(51) Int. Cl.[7] .................................................. B05D 1/00
(52) U.S. Cl. ...................................................... 427/384
(58) Field of Search ......................................... 427/384

(56) References Cited

U.S. PATENT DOCUMENTS

| | | | |
|---|---|---|---|
| 4,973,493 A | 11/1990 | Guire ............................ 427/2 |
| 5,002,582 A | 3/1991 | Guire et al. .................. 623/66 |
| 5,075,400 A | 12/1991 | Andrade et al. ......... 526/307.5 |
| 5,077,210 A | 12/1991 | Eigler et al. ................ 435/176 |
| 5,246,846 A | 9/1993 | Pittner et al. ............... 435/174 |
| 5,369,012 A | 11/1994 | Koontz et al. ............. 435/7.92 |
| 5,374,516 A | 12/1994 | Sutton et al. ................... 435/5 |
| 5,389,533 A | 2/1995 | von Gentzkow et al. ... 435/180 |
| 5,403,902 A | 4/1995 | Heilmann et al. .......... 526/260 |
| 5,405,766 A | 4/1995 | Kallury et al. .............. 435/174 |
| 5,436,147 A | 7/1995 | Pegg et al. .................. 435/181 |
| 5,482,996 A | 1/1996 | Russell et al. ............. 525/54.1 |
| 5,512,329 A | 4/1996 | Guire et al. ................ 427/508 |
| 5,663,318 A | 9/1997 | Pegg et al. ................. 536/24.3 |
| 5,741,551 A | 4/1998 | Guire et al. ............. 427/407.1 |
| 5,858,653 A | 1/1999 | Duran et al. .................... 435/6 |
| 5,861,319 A | 1/1999 | Lin et al. ..................... 436/527 |
| 5,866,387 A | 2/1999 | Ogino et al. ................ 435/179 |
| 5,986,066 A | 11/1999 | Barner et al. ............ 530/391.1 |
| 6,093,559 A | 7/2000 | Bookbinder et al. ........ 435/183 |
| 6,235,340 B1 | 5/2001 | Lee et al. .................. 472/2.12 |
| 6,465,178 B2 | 10/2002 | Chappa et al. .................. 435/6 |

FOREIGN PATENT DOCUMENTS

| | | | |
|---|---|---|---|
| EP | 913690 | * | 5/1999 |
| WO | WO 95/06251 | | 3/1995 |
| WO | WO 96/22966 | | 8/1996 |
| WO | WO 98/40741 | | 9/1998 |
| WO | WO 99/08717 | | 2/1999 |
| WO | WO 99/16907 | | 4/1999 |
| WO | WO 99/43688 | | 9/1999 |
| WO | WO 2001 / 94032 | * | 12/2001 |

* cited by examiner

*Primary Examiner*—Erma Cameron
(74) *Attorney, Agent, or Firm*—Dorsey & Whitney LLP

(57) ABSTRACT

Compositions and methods of preparing functional thin films or surface coatings with low non-specific binding are described. The thin films contain specified functional groups and non-specific binding repellant components. The thin films are either covalently bound to or passively adsorbed to various solid substrates. The specified functional group provides specified activity for the thin film modified solid surfaces and non-specific binding repellant components significantly reduce the non-specific binding to the thin film modified solid surfaces. Non-specific binding repellant components do not affect specified functional group's activity in the thin films. In these methods, specified functional groups are anchored to the solid substrates through a spacer. Surface coatings are also described having both non-specific protein binding properties combined with functional groups for specific binding activity thereby providing surface coating that specifically recognize target proteins but limit binding to non-specific protein.

10 Claims, 20 Drawing Sheets

US 6,844,028 B2

FUNCTIONAL SURFACE COATING

CROSS REFERENCE TO RELATED APPLICATIONS

This application claims the benefit of priority of U.S. Provisional Patent Application Ser. No. 60/301,223 filed on Jun. 26, 2001, entitled FUNCTIONAL SURFACE COATINGS WITH LOW NON-SPECIFIC BINDING PROPERTIES, which is incorporated herein by reference.

FIELD OF THE INVENTION

This invention relates generally to the field of surface coatings that impart desirable chemical, physical, and biological properties to a substrate material. In particular, this invention relates to surface chemistries designed to inhibit non-specific adsorption or binding of molecules, particles, or cells to a surface while also providing a means for immobilizing or entrapping specific molecules, capture agents, drugs, particles, or cells to or within that same surface. This invention further relates to coatings for application to a variety of chemically distinct substrate materials.

BACKGROUND OF THE INVENTION

Controlling the interactions between naturally derived or synthetic materials and biomolecule-containing fluids is of increasing importance in a variety of fields. For example, biomolecule interactions with a variety of substrate materials, i.e., surfaces, are central to numerous analytical systems, including immunodiagnostics, gene and protein microarrays, and microfluidic "lab-on-a-chip" devices. Analytical techniques such as capillary electrophoresis (CE), surface plasmon resonance (SPR), and quartz crystal microbalance (QCM) also intimately depend on biomolecule-surface interactions. Performance of biomedical devices including cardiovascular replacements (e.g., catheters, valves, stents), contact and intraocular lenses, shunts, filters, diaphragms, pumps, membranes, drug delivery devices and surgical components also depend on control of biomolecule-surface interactions. Maritime surfaces, including heat exchange units, ship-board components (e.g., hulls, superstructure), installations (pump derricks), docks, and environmentally exposed instruments also require control of biomolecule deposition (algae, fungus, microbial exudates) on their surfaces.

Of major common concern within these fields is the level of non-specific biomolecule (e.g., protein, organismal, nucleic acid) binding to target and device substrates. In non-sensing or non-diagnostic applications, this concern general focuses on surface-induced biofouling (deposition of biological material that compromises function). This is particularly problematic in biomedical devices and maritime applications. In medical, food, and environmental sensing and diagnostics, specificity, signal-to-noise ratios, and detection limits of a target analyte (e.g., polysaccharides, nucleic acid, drug, peptide or protein), often at limited concentrations in a milieu of non-target biomolecules (e.g., serum proteins), are limited by surface non-specific non-target (e.g., protein) binding on the substrate. Reduction or elimination of this non-specific binding noise will improve device performance, and enhance signal-to-noise ratios, detection sensitivity and specificity of many analytical systems.

Beyond analytical systems, the synthetic material-biological interface is central to the proper function of many biomedical devices. For example, non-specific binding of proteins at medical implant surfaces is believed to be at least partially responsible for triggering the foreign body response, which in turn can lead to device failure or rejection. This biofouling is also blamed for device infection incidence, thrombosis, and sensor deterioration over time in vivo. Alternatively, it has been hypothesized that implant surfaces that interact with target biomolecules in a specific manner can be used to stimulate natural healing, avoiding many adverse reactions from biofouling. In addition, numerous non-analytical and non-medical applications require direct control of surface-biological fluid interactions. Examples include non-fouling paints and anti-microbial coatings for industrial equipment, colloid and mineral handling systems, cooling systems, marine structures, and bioreactors used for production of biological products in vitro using biological components.

Improvements in these important fields all would benefit from development of improved surface chemistries where specific target binding, tethering or entrapment can be controlled versus non-specific deposition of undesired components. A core requirement of these surface chemistries is that the synthetic surfaces show reduced or limited non-specific binding (NSB) to non-targets, biomolecules, particles, or cells. NSB occurs through a variety of basic molecular-level adhesion mechanisms, including all combinations of electrostatic, hydration, hydrophobic, acid-base, dispersive and hydrogen bonding interactions. Soluble proteins, for example, generally ubiquitously and universally adsorb to a surface through combinations of these non-specific interactions, creating an adherent layer of biological material difficult to remove (a critical step in biofouling). Protein NSB often results in protein denaturation (loss of native structure) on surfaces that can prompt a cascade of additional NSB events (further adsorption of other proteins, cells, micro-organisms, etc., to the exposed interior of the denatured protein). This biofouling NSB cascade produces undesired infection, coagulation, inflammatory responses for biomedical implants, reduced signal-noise ratios for diagnostic assays and sensors, corrosion and deterioration for maritime and environmentally exposed structures, turbulence and reduced propulsion efficiency for maritime shipping, and undesired pressure drops and flow properties in capillaries, tubes and microfluidic chambers. Inhibition of protein and biomolecule NSB is thus an important performance feature in the design of improved synthetic materials that contact, function with, and operate in biological fluids.

While NSB to surfaces is most often undesirable, specific capture of designated biomolecules, particles, drugs or cells by binding at a target surface is often desirable. Examples include the specific binding of bioactive antibodies on a surface for immunoassay applications, specific binding of nucleic acid primers on a surface for polymerase chain reaction (PCR) or genetic assays (microarrays), and specific binding of growth factors or antibiotics to surfaces to promote or hinder cell growth, respectively. The goal of such specific binding to a surface is to bind only one designated type of molecule, particle, or cell, to the target surface and to do so in a manner that preserves the recognition activity and native structure and function of the specifically bound molecule, particle or cell.

Thus, functional surface chemistries are needed that (1) inhibit non-specific binding of unwanted molecules, particles, or cells to a treated surface; (2) inhibit non-specific binding of unwanted molecules, particles, or cells to a treated surface while promoting specific biomolecule, particle, or cell binding, to that same surface; or (3) that inhibit non-specific binding of unwanted molecules, particles, or cells to a treated surface while promoting specific and functionally or biologically active biomolecule, particle, or cell binding, to that same surface.

Several strategies have been employed to create surfaces with these desired low non-specific binding properties. These strategies typically involve selection of coating chemistry or surface functional groups that exhibit low NSB and then fixing them to an underlying substrate. The fixing step may be based on physical adsorption or on direct covalent linkage (chemical coupling). From a performance perspective, the layer must exhibit robust bonding to the underlying support while maintaining low-NSB properties to the environment.

Surface coating strategies based on synthetic polymers have been the focus for development of most non-fouling coating applications. A. S. Hoffman, "Non-Fouling Surface Technologies," *Journal of Biomaterials Science: Polymer Edition* 10, no. 10 (1999): 1011–1014; Poly(ethylene glycol): Chemistry and Biological Applications, ACS Symposium Series 680, J. Milton Harris and Samuel Zalipsky, Eds., American Chemical Society, 1997. Hydrophilic, polar, electrically neutral polymers such as polyethylene glycol (PEG) derivatives have received significant attention because of their long-acknowledged abilities to reduce protein NSB from solutions in coated formats. The challenge has been to effectively fix these and other similar water-soluble polymers to useful substrate materials at densities sufficient to impart effective NSB through contiguous coating. One approach has been to physically adsorb hydrophilic-hydrophobic block copolymers to hydrophobic supports. Hydrophobic interactions between the substrate and hydrophobic polymer block are sufficient to attach coating polymer molecules to the substrate while presenting the hydrophilic, low-NSB block to the aqueous surroundings. U.S. Pat. Nos. 5,075,400 and 6,093,559. Problems with these physically adsorbed films, however, include reversible polymer desorption, particularly in challenging liquid environments (e.g., high salt, non-neutral pH, elevated temperature, shearing flow conditions, etc.), and the ability to achieve reproducible adsorbed densities effective to limit NSB.

Another approach to creating surfaces with low non-specific binding properties relates to the covalent coupling of low-NSB coating polymers to the target surface. PEG, for example, can be covalently grafted to substrates through reactive end groups introduced to the PEG molecule. U.S. Pat. No. 5,512,329. Azido chemistry and quinone chemistry are two photo-reactive end group examples for such fixation to polymer substrates. A disadvantage of this approach is that it is confined to coating particular types of polymer supports where this coupling chemistry is effective and available. Attachment to interesting inorganic substrates such as glass or metals requires some intermediate substrate attachment layer, which adds to the cost, time consumption, and overall effectiveness of the coating procedure. One particular example of this procedure relies on PEG-silanes used to create coatings on active metal oxide surfaces (glass, silica, titania, alumina and others). In this system, a PEG molecule is derivatized with alkoxysilane or chlorosilane terminal reactive groups. Hydrolysis and chemical condensation of the reactive silanes presumably serve to anchor the PEG molecules to oxide substrates such as glass or silicon oxide with exposed surface silanol groups. Despite their initial promise, PEG-silane surfaces are difficult to reproduce practically. It is believed that the terminal alkyl silane reactive groups hydrolyze in solution and then react with each other in the bulk solution, prior to attachment to the substrate, yields poorly defined films (reactive groups cross-react with each other rather than to anchor the PEG-silane to the surface) allowing for a partial physically adsorbed polymer coating mixed with some fraction of chemical attachment. Control of this for reliable coating and low NSB is difficult.

An alternative to forming a polymer film for blocking non-specific binding on a substrate is to inhibit the non-specific binding to the substrate with a biomolecule-blocking step (masking). The most common practice in this respect is to pre-adsorb substrates with soluble bovine serum albumin (BSA), casein, or serum. These proteins (or proteins in the serum) adsorb strongly to most surfaces from aqueous solution, providing an adsorbed protein layer that minimizes subsequent non-specific binding of other biomolecules. While such protein blocking has proven to be functionally effective, the blocking step is time consuming, labor intensive, and subject to reproducibility problems. In addition, there is a general desire to move away from the use of animal and serum-derived products in surface chemistry applications for safety reasons.

Thus a perceived improvement in the art is a solid-phase surface coating capable of consistently strong, direct and effective attachment to a variety of substrate materials. The surface should reliably exhibit low non-specific binding properties and should be easy to use (i.e., should require no blocking steps). Ideally, the surface chemistry should also provide a means for immobilizing chemically reactive coupler or functional groups on the surface, which in turn exhibit strong specific attachment properties for desired target immobilization onto surfaces. Against this backdrop of technical challenges and current limitations in the field, the present invention has been developed.

SUMMARY OF THE INVENTION

Embodiments of the present invention are directed at novel surface chemistries and methods of preparing functional solid-phase coatings and surfaces with improved properties both limiting NSB and enabling specific binding. The present invention provides for robust coating bonding over various substrates, including oxide, metal, composite, ceramic, and polymer substrates while simultaneously imparting surface properties that substantially inhibit non-specific binding of solutes from external milieu.

Without wishing to be bound to a particular theory, it is considered that the interaction between the various components of the surface chemistry, described in more detail below, provide the strengths and benefits of a novel surface coating with robust attachment to a variety of chemically distinct solid phase substrates. The chemistry of the coating substantially reduces dependence upon a single attachment mechanism (i.e., silane coupling, physical adsorption, photoreaction, chemical attachment, etc.). Instead, the multifunctional nature of the coating chemistry provides multiple likely attachment mechanisms, including covalent attachment to oxide, ceramic and polymer substrates, crosslinking within the coating, and adsorption via hydrophobic interactions, acid-base chemistry, hydrogen bonding, etc., which act in combination or synergistically to stabilize the coating on the substrate and reliably present the desired surface properties. Importantly, chemical cross-linking within the applied coating itself is believed to augment the coating cohesive character, coating-substrate interactions, and add to the robustness of substrate attachment.

The present invention promotes formation of a functional surface coating. The term "functional" is used herein to describe the ability to perform a specific chemical or analytical task. For example, one class of functional surfaces can provide specific affinity binding or ligand-receptor binding capabilities with designated solutes. For example, a surface can be created that presents biotin groups consistently at the surface. Biotin groups exhibit a highly specific, high affinity binding interaction with streptavidin protein molecules and their mutants. The functional surface in this example, therefore, is a biotinylated, low background NSB coating where function is defined by the ability to specifically bind streptavidin.

In another embodiment of the present invention, the functional surfaces are designed to inhibit all molecular binding interactions to the coating. In this case, the specific functional task is to be interfacially inert. A manifestation of such "inert" function could be a surface that presents effective densities of methoxy-capped ethylene oxide oligomers or polymers. Such surface groups generally do not form covalent linkages, generally do not show affinity binding properties to proteins, cells, or particles, and in general resist adsorption of biomolecules and other soluble species. In the context of the present invention, these inert groups are incorporated directly into the underlying low-background NSB coating invention.

The present invention embodies a coating architecture comprising designated functional surface groups (e.g., methoxy-PEG or biotin) integrated with a cross-linked, low-NSB coatable matrix. The surface functional groups are covalently coupled to the coating matrix through spacer molecules selected to provide conformational flexibility and to be inert to non-specific adsorption. The low-NSB matrix comprises these spacers and other so-called matrix-forming molecules that have been cross-linked into the coatable film. Exemplary matrix-forming molecules include polysaccharides (dextran), ethylene oxide-containing oligomers (linear, block, dendritic or star polymer forms), block co-polymers (Poloxamer®, Pluronics®), and non-ionic surfactants (Tween®, Triton®). The coating architecture is believed to rely on a combination of both physical and chemical cross-linking mechanisms. In addition to physical entanglement of large molecules in the matrix, hetero- or bi-functional, reactive cross-linker molecules may also be included and chemically activated in the coatings. Covalent cross-linking is believed to occur both within the coating matrix and to the substrate. An advantage of using hetero- and bi-functional cross-linkers in this invention is that the coating can be effectively applied and cross-linked to a variety of chemically distinct substrate materials with or without specific surface attachment. The coating described in this invention provides robust attachment both within itself and also to various substrates.

The present invention provides methods of preparing a functional surface coating using the components with the described functions. The methods include providing a substrate with an effective amount of an active component, providing an effective amount of a cross-linking component and providing an effective amount of a matrix-forming component. The active component, the cross-linking component and the matrix-forming component are incorporated onto the substrate, and integrated with each other to create the stable, robust functional surface improvement.

The present invention also provides a functional surface for performance of immuno, genetic, microbial, cellular, particulate and other biochemical or target analyte binding assays. Thus, a non-specific binding matrix is attached to a substrate and an active component is integrated into the non-specific binding matrix to impart these coating selectivities for various assay formats.

In addition, embodiments of the present invention provide functionally inert surface coatings for medical implant devices for effectively limiting host rejection of the medical implant device through attached ligands, incorporated drugs, and reduced NSB responsible for biofouling of such devices in- or ex-vivo.

These and various other features as well as advantages which characterize the invention will be apparent from a reading of the following detailed description and a review of the appended claims.

BRIEF DESCRIPTION OF THE DRAWINGS

FIG. 14(a) shows fluorescence detection of Cy 5 Streptavidin bound to 3' biotin labeled oligonucleotide. Signal intensities are reported in relative fluorescence units. Data were obtained from three representative runs and error bars represent one standard deviation.

DETAILED DESCRIPTION OF PREFERRED EMBODIMENTS

The features and other details of the preferred embodiments of the present invention will now be more particularly described. It is to be understood that the particular embodiments of the invention are shown by way of illustration and not as limitations of the invention. The principle features of this invention can be employed in various embodiments without departing from the scope of the invention.

Figure 1:
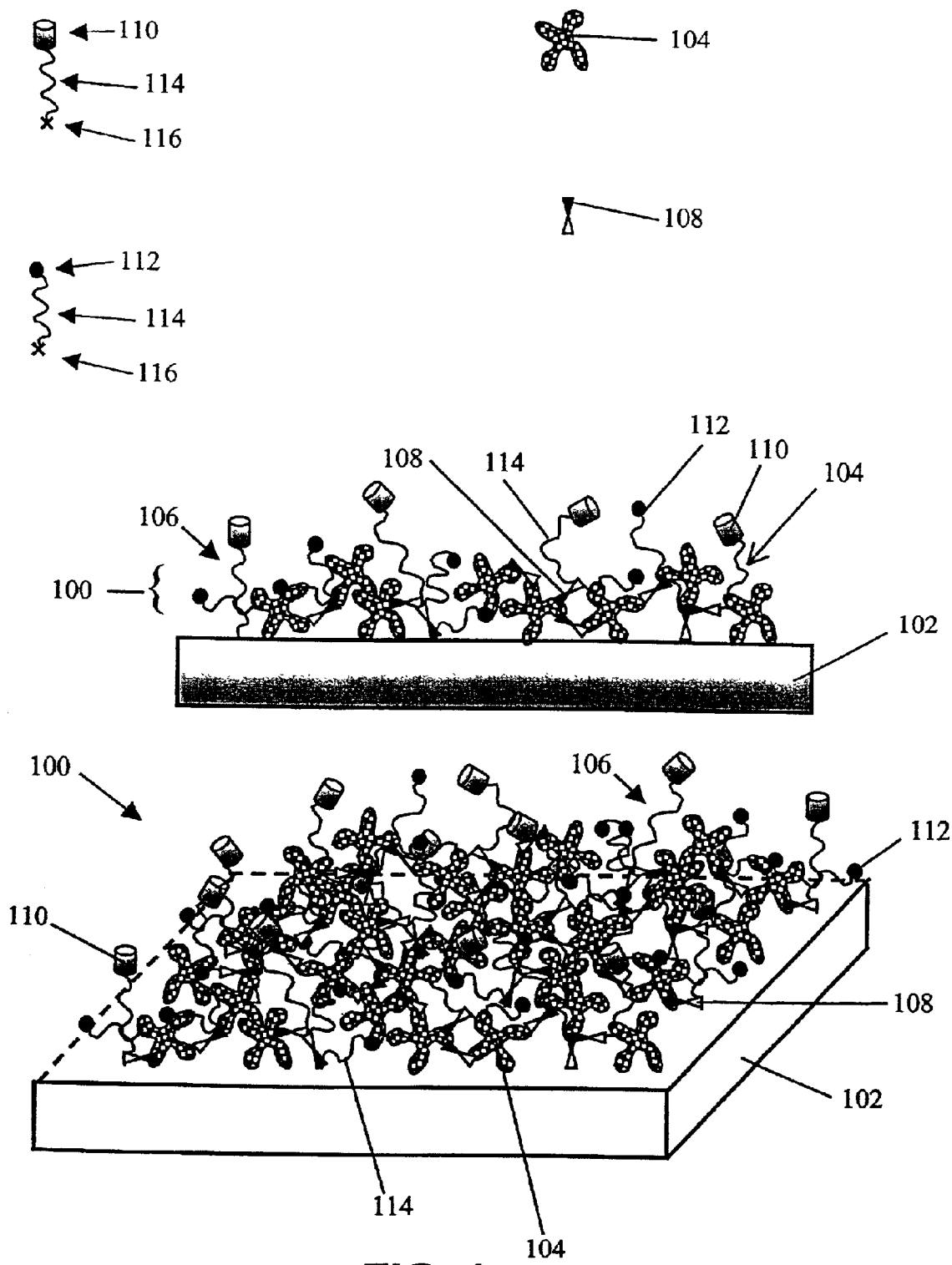
FIG. 1 is a diagrammatic depiction of a functional surface, in accordance with one embodiment of the present invention. The coatable embodiment comprising an active component, a cross-linking component, and a matrix-forming component are schematically depicted to represent their function within the integrated coating on the substrate. Note that a schematic representation of the components comprising the present invention is shown at top, a cross-sectional representation of possible coating architecture is shown in the middle, and a three-dimensional representation of possible coating architecture is shown at bottom.

The present invention provides methods and compositions for the preparation of multi-component, multi-functional thin film coatings 100 applied to and stabilized upon a variety of substrates 102 (see FIG. 1). These coatings 100 substantially inhibit non-specific binding or adsorption of non-target proteins, e.g., fibrinogen, undesired enzymes and antibodies, undesired nucleic acids, polysaccharides, particulate solutes, microbes, cells, colloids, and the like (collectively termed non-target analytes), to the coated substrate. The present invention also describes such surfaces stabilized upon a variety of substrates 102 that provide for very low non-specific binding and, if desired, high specific binding and increased assay selectivity and sensitivity.

A diagrammatic depiction of a multi-component, multi-functional surface coating 100 according to one embodiment of the present invention is shown in FIG. 1. FIG. 1 illustrates the components of the method and apparatus of the present invention and their believed interactions. As shown in FIG. 1, a substrate 102 is provided with a low non-specific binding matrix 104 affixed upon the substrate 102 and an active component 106 physically entangled and covalently bound within the applied non-specific binding matrix 104. The methods, coatings, compositions, use and kits, according to preferred embodiments of the present invention, are described in more detail below.

Methods of the present invention are directed to the preparation of functional surfaces 100 capable of either or both specific binding and reduced non-specific binding to a target substrate 102. The coating method includes providing effective amounts of an active component 106, a cross-linking component 108, and a matrix-forming component 104. These three general components are incorporated onto the substrate, thereby creating and comprising the functional surface coating 100 and imparting the properties described by the invention.

The term "functional surface" 100 is used herein to describe a surface that employs specific chemical groups to selectively bind desired target molecules, particles, cells, and the like (collectively called target analytes), from external milieu, and/or to collectively reject undesired molecules, particles, cells, and the like (collectively called non-target analytes), from the surface. By this definition, one class of functional surfaces 100 provides specific binding capabilities through the incorporation of specific functional groups 110 at the surface. An example is a biotinylated surface that exhibits high avidin binding activity (typically in the range of 300 to 500 $ng/cm^2$ of avidin) and low NSB of other biologics, particulates, and solutes (typically in the range of 0.01 to 50 $ng/cm^2$). The term "functional surface" is also used herein to describe chemical groups or surface compositions that exhibit inherently low protein or particulate binding or adsorption in the range specified (typically around 0.01 to 50 $ng/cm^2$). Thus, the "function" in this class of surfaces is to be substantially inert to protein, cell, microbe and particulate adsorption. An example of such inert functionality is a surface that presents methoxy-capped ethylene oxide oligomers or polymers. These inert surface groups 112 generally do not form covalent linkages, generally do not show affinity binding properties, and in general tend to resist adsorption of biomolecules, particulates, cells, microbes, and other soluble species (non-target analytes).

For the purposes of this application, "effective amount" is defined as an amount of a specified coating component that, when combined with the other coating components, yields a coating matrix that meets specified performance standards for the desired application (e.g., assay or implant coating). These performance standards are defined for both "low non-specific binding or adsorption" ("low-NSB") and "highly selective specific binding," as described below.

For the purposes of this application, the terms "low non-specific binding," "low non-specific adsorption," and "low-NSB" are defined relative to the current method of bovine serum albumin (BSA) blocking, i.e., masking. BSA-blocking is a process in which the soluble serum protein, bovine serum albumin, is physically adsorbed from solution to a substrate material prior to the use of that substrate in a biological fluid setting. This pre-adsorbed BSA layer serves to inhibit additional solute or particulate adsorption on the substrate. The BSA-blocking method represents a practical state-of-the-art process for the inhibition of non-specific binding or adsorption to a variety of substrates, particularly in the context of biochemical assays. Thus, for the purposes of the present invention, a coating formulation that inhibits NSB in a manner similar to or superior to BSA-blocking, without the requirement of a BSA-preadsorption or any equivalent blocking step, is herein considered to be a low-NSB surface.

The "highly selective specific binding" performance standard is also defined in a comparative manner. For the purposes of this application, a surface is considered to be highly selective when the specific binding group incorporated in the surface is able to selectively bind target (analyte) species from a complex milieu, when a similar surface lacking such specific binding groups shows little or no capacity to specifically bind target species (analytes). For example, a biotinylated surface is said to be highly selective relative to its non-biotinylated counterpart when significant, measurable quantities of avidin or streptavidin are bound to the former and not to the latter under the same binding conditions.

A final performance standard is the combination of "no selectivity" and low-NSB. In this case, no binding or adsorption is desired, either specific or non-specific. Again, performance is defined relative to a competing method such as BSA-blocking.

The incorporation or affixing step of the surface coat 100 onto a substrate 102 preferably comprises combining effective amounts of active component 106, a cross-linking component 108 and a matrix-forming component 104 into a coatable mixture. This coatable mixture is applied to the substrate and cured to yield the stable, robust surface. Coating mixtures may also include other non-covalently attached functional groups, for example streptavidin, which becomes entangled within the matrix.

The methods of the present invention preferably include combining the active component, matrix-forming component, and cross-linking component in a carrier solvent or solvent mixture. The range of component concentrations used depends on the particular coating method chosen. Selection of solvent also depends on component chemistry, the coating method and choice of substrate material, with factors such as solvent surface tension, solubility parameter, viscosity, and reactivity with the chosen substrate influencing solvent selection.

Active Component for use with the Present Invention

Typically, embodiments of the active component 106 of the present invention include a functional group 110, a spacer group 114 and a binding group 116 (see FIG. 1). Note that where no specific binding is required, an inert functional group 112 can be inserted in place of the functional group 110.

In more detail, the term "active component" is intended to signify a bifunctional reactive molecule that includes at least one reactive group (for example 116) at one end of the molecule and at least one functional group (for example 110 or 112) at either end of the molecule. The distance between the two groups can be varied by varying the length of the spacer group 114 to provide the desired attributes as defined by the final product required by a person skilled in the art. As previously described, the active component 106 preferably includes specific chemical parts representing the functional group, spacer, and binding group. Specific definitions of these terms are provided below. The active component 106 is preferably a combination of these groups; however, it is to be understood that the active component need not necessarily comprise three distinctly separate groups. It is possible that one group can act both as a functional group and a spacer group, for example. It is also possible, for example, that the functional group (for example 110 or 112) and the reactive group 116 have the same chemical structure (e.g., a homo bifunctional active component). The active component need only perform the function described with respect to each group of the active component as discussed below, with minimal parts needed to accomplish these objectives.

The term "functional group," 110 as used herein, is intended to include those groups that can generally interact with and form an association (both covalent and non-covalent) with target species external to the surface while generally not associating with non-target species. The term "functional group" may also refer to those groups that are essentially inert to binding and adsorption of any or all species in external milieu, referred to as an inert functional group 112.

For surfaces designed for specific binding applications, functional groups 110 include but are not limited to chemically active groups, receptor or ligand groups, and chelators capable of selectively binding desired target species. More specific examples of functional groups 110 include but are not limited to, for example, biotin, N-hydroxy succinimide esters, nitrophenyl esters, carboxylates, vinyls, vinylsulfone, metal chelates, glutathione, streptavidin, nitrenes, acrylate groups, phenylboronic acid, nitrolotriacetic acid (NTA), imidodiacetate (IDA), salicylhydroxamic acid, hydroxyl groups (—OH), amine groups (—$NH_2$), imine groups (—NHR) carboxylic acids (—COOH), aldehydes (—CHO), ketones (C=O), esters (—COOR), ethers (—C—O—C), amide groups (—$CONH_2$), imides (—CONHR), cyanides (—CN), hydrazides (—$NHNH_2$), succinimides (—$ONC_4O_2$), maleimide, thiols (—SH), halides (-X), silyl (—SiH), azido groups (—$N_3$), phenyl groups, sulfonates ($SO_3^-$), isothiocyanate, isocyanate, epoxides, nitrobenzyls, oxazoline, acid chloride, chloroformate, disulfide pyridyl, azlactone, cyanogen bromide, fluoroarenes, fluorocarbons, disulfides, isocyanides, sulfaamido, sulfate, heparin, peptides, nucleotides, polynucleotides, organic silicon compounds and organic phosphate (phosphoamidite) compounds.

For surfaces on which little or no specific surface binding is desired, inert functional groups 112 include non-reactive chemical groups such as, ethylene glycol oligomers, acrylamides, pyrollidones, poly- and mono-saccharides and polar synthetic polymers.

Choice of the functional group is within the skill of the art, based on known binding parameters of and derivatives of the functional group(s) appropriate for each use. Thus, the active component can be designed to specifically or non-specifically select and associate with chosen target analytes from external milieu.

The term "spacer," 114 as used herein, is intended to include those moieties that serve to separate the functional group 110 or inert functional group 112 from the binding group 116 of the active component 106. Typically, the length of the spacer group 114 is sufficient when the functional group and binding group can perform their respective functions without physical or chemical interference from each other. The spacer links the functional group to the binding group and also preferably separates the functional group a distance away from the coated solid substrate 102. This spacer 114 increases the accessibility of the functional group 110 to target species and reduces the steric hindrance from or binding interference with the solid substrate 102.

It is preferable that the spacer 114 is one consistent length that provides all functional groups with the same activity; however, this is not required. Example spacers include, but are not limited to, hetero-, bi-functional or multi-functional small molecules or polymers. These molecules can form covalent bonds or stable films upon solid substrates and, at the same time, provide functional groups for specifically binding target species from external milieu. For example, bi-functional, linear, star-shape, and comb-like PEGs (oligomers or polymers), polyethylenimines, polystyrene, polysiloxanes, polyurethanes, proteins, poly(amino acids), polyphosphazenes, telechelic block copolymers (Pluronics®), polyacrylates, polyacrylamides, polymethacrylates, polysaccharides, dendrimers, hyper-branched polymers, macromonomers, and cross-linking or heterobifunctional alkyl-linked coupling reagents are suitable spacers.

The term "binding group," 116 as used herein, is intended to include those moieties that can bind the active component 106 to the coating matrix 100 and/or to the underlying support 102. The binding group 116 is preferably selected to covalently bind the active component to the coating matrix or to the substrate. The binding group can also react with itself in the form of cross-linking. Examples of the binding group for use in the present invention include, but are not limited to, silanes, methacrylates, disulfides, disilazanes, sulfhydryls, acrylates, carboxylates, activated esters, other active leaving groups, isonitriles, isocyanates, phosphoamidites, nitrenes, epoxides, hydrosilyl, esters, arenes, azido, amine, nitrile, vinyl groups, alkylphosphonates, and known surface-coupling reactive species known to those skilled in the art of chemical coupling to surfaces.

In a preferred embodiment, the active component 106 is produced by combining an amount of a reactive chemistry carrying the binding group portion, such as an amino-terminated alkyl silane, with a spacer bearing a terminal functional group, such as biotin-PEG-$CO_2$—N-hydroxysuccinimidyl (NHS-PEG-biotin). This combination results in an active component having a terminal silane available to act as the reactive or binding group, a PEG portion acting as a spacer group, and biotin serving as the functional group. The active component has the general molecular formula X-PEG-Y, where X is the functional group and Y is the binding group.

Although a list of possible functional groups is provided above, example preferred functional groups include, but are not limited to biotin, N-hydroxysuccinimide, vinylsulfone, metal ion chelates (e.g., $Ni^{2+}$-NTA), glutathione binding group, amino, aldehyde, epoxy, mercapto, maleimide, heparin, methoxy, and sulfonate. Example preferred binding groups include, but are not limited to silane, azide, acrylate, aldehyde, isocyanate, phosphonate, and epoxy.

The methods of the present invention preferably include forming a 0.001 mol/liter to 0.1 mol/liter solution of active component 106 in a solvent, more preferably 0.005–0.02 mol/liter solution of active component in a solvent, and most preferably 0.01 mol/liter solution of active component in a solvent. As noted above, the active component 106 is preferably a molecule of the form X-PEG-silane, wherein: X is a functional group such as biotin, vinylsulfone, or an N-hydroxysuccinimidyl ester; PEG is a polyethyleneglycol polymer, preferably of molecular weight 2000 to 5000 atomic mass units; and silane is a hydrolyzable silane precursor group (e.g., trialkoxy or trichlorosilane).

In a preferred embodiment, the active component 106 is a biotin-PEG-silane molecule formed by reacting biotin-PEG—$CO_2$—N-hydroxysuccinimide (biotin-PEG-NHS, molecular weight 3400, e.g., Shearwater Corp., OH2Z0F02) with an amino-terminated alkoxysilane ((3-trimethoxysilylpropyl)-diethylenetriamine, e.g., Gelest, SIT8398.0) at a 1:1 mole ratio in the chosen solvent. The reaction is preferably carried out at room temperature for two hours. The N-hydroxysuccinimide group on the biotin-PEG-NHS reacts reliably with the terminal amine on the aminosilane to yield the biotin-PEG-silane active component. An example solvent for the active component is N,N-dimethylacetamide (DMAC, Aldrich 27,055-5).

In another preferred embodiment, two active components 106: biotin-PEG-silane and methoxy-PEG-silane, are combined in the coating mixture. By diluting the biotin functional group in "inert" methoxy groups, increased biotin binding activity of bound streptavidin can be achieved. The first active component is the biotin-PEG-silane, molecular weight 3400 described in the previous paragraph. The second active component is a methoxy-PEG-silane, formed by reacting methoxy-PEG—$OCH_2CH_2$—$CO_2$—N-hydroxysuccinimide (methoxy-PEG-NHS), preferably of molecular weight less than 3400, most preferably molecular weight 2000 (e.g., Shearwater Corp., 2M4MOD01), with an amino-terminated alkoxysilane ((3-trimethoxysilylpropyl)-diethylenetriamine, e.g., Gelest, SIT8398.0) at a 1:1 mole ratio in the chosen solvent.

In another preferred embodiment, the active component is a methoxy-PEG-silane, preferably formed by reacting methoxy-PEG—$OCH_2CH_2$—$CO_2$—N-hydroxysuccinimide, molecular weight 5000 (e.g., Shearwater Corp., 2M4M0H01) with an amino-terminated alkoxysilane ((3-trimethoxysilylpropyl)-diethylenetriamine, e.g., Gelest, SIT8398.0) at a 1:1 mole ratio in the chosen solvent.

In another preferred embodiment, the active component 106 is a vinylsulfone-PEG-silane, preferably formed by reacting vinylsulfone-PEG—$CO_2$—N-hydroxysuccinimide, molecular weight 3400 (e.g., Shearwater Corp. 2Z5B0F02) with an amino-terminated alkoxysilane ((3-trimethoxysilylpropyl)-diethylenetriamine, e.g., Gelest, SIT8398.0) at a 1:1 mole ratio in the chosen solvent.

In another preferred embodiment 106, the active component is an NHS-PEG-silane, preferably formed by reacting a bis-functional N-hydroxysuccinimidyl ester of PEG (SPA-PEG-SPA, molecular weight 3400, e.g. Shearwater Corp., 4M4M0F02) with an amino-terminated alkoxysilane ((3-trimethoxysilylpropyl)-diethylenetriamine, e.g., Gelest, SIT8398.0) at a 2:1 mole ratio in the chosen solvent. In another preferred embodiment, the active component 106 is a COOH-PEG-silane, preferably formed by reacting COOH-PEG-N-hydroxysuccinimide, molecular weight 3400 (e.g., Shearwater Corp., 0Z2Z0F12) with an amino-terminated alkoxysilane ((3-trimethoxysilylpropyl)-diethylenetriamine, e.g., Gelest, SIT8398.0) at a 1:1 mole ratio in the chosen solvent.

Cross-Linking Component and Matrix Forming Component for use with the Present Invention The "cross-linking component" 108 of the present invention is defined herein as a reactive molecule with multiple reactive moieties that when activated by appropriate stimulus, provides cross-linked stabilization within the film 100 as well as covalent or adsorptive film attachment to or upon various solid substrates 102.

In one embodiment, the cross-linking component 108 includes the alkylsilane and sulfonylazide reactive end groups, which when combined create dual reactive functionalities that upon curing proceed to form spontaneous cross-links both within the coating and to various substrates 102. Exemplary crosslinking groups include molecules that combine groups from the list including: methacrylates, acrylates, epoxides, silanes, perfluorophenyl azides, aryl azides, bis-nitrenes, acyl azides, azidoformates, sulfonyl azides, phosphoryl azides, diazoalkanes, diazoketones, diazoacetates, beta-keto-alpha-diazoacetates, aliphatic azo, diazirines, ketenes, photoactivated ketones, dialkyl peroxidases, diacyl peroxidases, or quinones. As an example, 6-azidosulfonylhexyltriethoxysilane is provided, which includes silane groups able to form covalent bonds with reactive hydroxyl groups present on surfaces of substrates such as a oxidized polymers, metal oxides, silicon wafers, silicates, titanates, aluminates, or glasses. The silane groups can also cross-linked with each other or with other silane groups, forming a three-dimensional cross-linked matrix. The azidosulfonyl group can form covalent bonds with aliphatic and aromatic compounds both on the substrate 102 and/or within the coatable multi-component matrix 104.

The term "matrix-forming component," 104 as used herein, is intended to include those molecules known in the art to have physical characteristics of providing low non-specific binding properties towards biological (e.g. proteins, polysaccharides, cells, and bacteria) and non-biological (e.g. particulate, colloidal, ionic, siliceous, and carbonaceous) compounds. Ostuni, E.; Chapman, R. G.; Holmlin, R. E.; Takayama, S.; Whitesides, G. M. *Langmuir*, 17: 5605–5620 (2001). Such matrix-forming molecules typically include one or more of the following characteristics: such molecules can be polar, hydrophilic, and electrically neutral, are hydrogen bond acceptors, and typically exhibit conformational flexibility.

Examples of the matrix-forming component 104 include, but are not limited to, polyoxyethylene-based surface-active substances, including polyoxyethylene sorbitan tetraoleate (PST), polyoxyethylene sorbitol hexaoleate (PSH), polyoxyethylene 6 tridecyl ether, polyoxyethylene 12 tridecyl ether, polyoxyethylene 18 tridecyl ether, Tween® surfactants, Triton® surfactants, and the polyoxyethlene-polyoxypropylene copolymers such as the Pluronic® and Poloxamer® product series (from BASF). Other matrix-forming components include dextrans, linear PEG molecules (MW 500 to 5,000, 000), star-shaped PEG molecules, comb-shaped and dendrimeric, hyperbrached PEG molecules, as well as the analogous linear, star, and dendrimer polyamine polymers, and various carbonated, perfluorinated (e.g., DuPont Zonyl® fluorosurfactants) and siliconated (e.g, dimethylsiloxane-ethylene oxide block copolymers) surfactants. Matrix-forming components 104 of biological origin include casein, serum dilutions, bovine serum albumin, glycolipids and lipids, heparin and related glycosaminoglycans, muscin and polysaccharides (dextrans, hyalurons, sepharose, cellulose, agarose, chondroitins, chitosans).

A solution of cross-linking component 108 and matrix-forming component 104 is also formed in a carrier solvent. As noted above, the matrix-forming component 104 is preferably a linear or branched polyoxyethylene-containing surfactant. Most preferably, the matrix-forming component 104 is polyoxyethylene sorbitan tetraoleate (PST, e.g., Aldrich 46,639-5). The matrix-forming component is preferably dissolved to provide a 0.01 to 5% (vol/vol) solution in the final coating mixture. More preferably, the matrix-forming component has a concentration of 0.5 to 2% in the final coating mixture. Most preferably, the matrix-forming component 104 concentration is 1% (vol/vol) in the final coating mixture.

As noted above, the cross-linking component 108 is preferably a bi-functional chemically reactive compound, and more preferably a hetero bi-functional molecule with azido functionality on one end of the molecule and alkyl silane functionality on the other end. Most preferably, the cross-linking component 108 is an azidosilane (6-azidosulfonylhexyl-triethoxysilane, 95%; Gelest, e.g., SIA0780.0). The cross-linking component is preferably dissolved to give a 0.001 to 0.5 mol/liter solution, and more preferably, 0.005 to 0.1 mol/liter solution in solvent. Most preferably, the cross-linking component 108 is dissolved to provide a 0.02 mol/liter solution. The preferred solvent for the cross-linking component/matrix-forming component mixture is dimethylsulfoxide (DMSO, e.g., Aldrich 47,230-1), although other solvents are envisioned.

Coating Solutions for use in the Present Invention

In use, the coating solutions 100 of the present invention are prepared by combining an active component solution of the present invention with the cross-linking component 108/matrix-forming component 104 mixture of the present invention at a variety of different volume ratios. The most preferred ratio is approximately 1:4 volume ratio of active component solution to cross-linking/matrix-forming component solution. The most preferred final component concentrations in the coating solution are: 0.002 mol/liter active component (e.g., biotin-PEG-silane), 0.009 mol/liter matrix forming component (polyoxyethylene sorbitan tetraoleate) and 0.0183 reactive component (azidosilane).

Note that the most preferred final concentration depends in part on the coating method to be employed and the desired coating thickness. The most preferred concentrations described above are associated with a spin-coating fabrication operation. However, other active component to cross-linking/matrix-forming ratios and final concentrations are envisioned to be within the scope of the present invention as long as the combinations provide useful coating solutions that exhibit the desired specific/non-specific binding characteristics. Note also that other target proteins or analytes may be included in the combination of active component, cross-linking component, and matrix-forming component. For example, streptavidin may be mixed with biotinylated active components to form a streptavidin-biotin surface, thereby providing a surface coating having streptavidin immobilized within the coating matrix (termed a streptavidin-biotin surface, see Example VIII below).

Substrates for use in the Present Invention

The term "substrate," 102 as used herein, is art recognized and is intended to include any surface capable of being coated with the combination of components of the present invention. Suitable substrates 102 include refractive, transparent, adsorptive and opaque solid-phase materials. They include, but are not limited to metals, such as, gold, platinum, silver, copper, iron, aluminum; polymers: such as polystyrene, polysulfone, polyetherimide, polyethersulfone, polysiloxane, polyester, polycarbonate, polyether, polyacrylate, polymethacrylate, cellulose, nitrocellulose, perfluorinated polymers, polyurethane, polyethylene, polyamide, polyolefin, polypropylene, nylon, hydrogels, and related blends and copolymers; non-metals, such as silica, silicon dioxide, titanium oxides, aluminum oxides, iron oxides, carbon, silicon, various silicates and other glasses, for example soda-lime glass, ceramics and sol-gels. Advantageously, the surface chemistry of the present invention secures itself over all these classes of substrates 102 and their derivatives and modifications. Again, it is believed that the cross-linking and other reactions within the matrix-forming component, reactive component and active component facilitate the stability of the non-specific binding matrix upon and over the substrate 102 without unnecessary covalent attachment to the substrate.

Note that some substrates 102 for use in the present invention may require cleaning steps and drying steps, oxidation steps or other procedures known in the art to facilitate the effective uniform coating interaction between the coating solution 100 and the target substrate 102. For example, glass slide substrates are typically "primed" by rinsing in high purity water, soaked in an alkaline glass cleaner, sonicated for a period of approximately 15 minutes in the cleaner, soaked in high purity water and finally blow dry under $N_2$ gas. Other substrate preparation procedures are discussed in the Examples or would be known to one of skill in the art.

Application of the Coating Solution to a Substrate

The coating mixture, as described above, is applied to a target substrate 102. Preferably the application of the coating solution to the substrate 102 is accomplished by spin coating, dip coating, spray coating, or any other type of coating or application method known to those of ordinary skill in the art. More preferably, the coating mixture is spin coated onto the substrate. Most preferably, the coating mixture is spin coated onto the substrate by applying 0.5 ml of the coating mixture to a substrate in a spin coater (e.g., Laurell Model WS-200-4NPP/RPM/HSP-8K/VAC) and spinning at 3500 to 5000 rpm for 90 seconds. Note that in certain applications a second, and sometimes third, coat or application of the coating mixture to the substrate is performed. These additional coating applications allow the thickness of the coating mixture layer to vary. Coating thickness on a target substrate is typically from about 5 to 200 nm, and is preferably about 20 to 30 nm. However, coatings can be of other thickness, as long as the coating is sufficient for performing the functions of the herein described present invention.

Note that the combination of the above described components provide coatings 100 that exhibit performance superior to the same coatings comprising subsets of the components. As shown in Example XV below, embodiments of the present invention operate optimally when all the above-described components (active component 106, cross-linking agent 108, and matrix forming agent 104) are present in the coating surface 100. However, it is envisioned that embodiments of the present invention may exclude one of the above components and still maintain some level of function, albeit a function (specific and non-specific binding) at a potentially non-optimal manner.

Curing of Surface Coated Substrate Targets

Once coated, curing, using known methods, stabilizes the coating onto the substrate. Preferably, the curing step is thermal activation in a vacuum oven. More preferably, the curing step includes a room temperature evacuation step in which the pressure within the vacuum oven is pumped down to a pressure of 150 mm Hg (absolute) for a period of 30 minutes, after which the oven is heated to 40° to 140° C., most preferably to 70° C. The total thermal curing step takes approximately one hour in this method. The curing temperature and time depend in part on the physical properties of the substrate material. Hence, shorter or longer curing times may be required dependent on the temperature and physical properties of the substrate 102. The coated surfaces are then allowed to cool to room temperature. This multi-step curing process is beneficial because it provides solvent removal and sufficient reaction time and temperature to form a robust, adherent functional coating 100.

The curing step stabilizes the functional surface invention for use. Note that the curing step can be by thermal activation (discussed above), photo activation, chemical activation or any other type of curing that creates cross-linking within the functional surface as well as bonding to the substrate. Thermal activation includes, for example, heating in an oven, photo activation includes, for example, irradiation with ultraviolet light, and chemical activation includes, for example, submersion in water, chemically facilitating cross-linking Chemical cross-linking may also proceed without external stimulus, for example through aging processes such as condensation. Any other form of chemical and physical transformation or curing can be used as known by those of ordinary skill in the art.

Example Binding Assays for use with the Present Invention

In one embodiment of the present invention, a functional surface 100 for performance of a biochemical or bioanalytical binding assay is provided. The functional surface comprises a general base composition tailorable to specific applications by changing appropriate functional group chemistries within the coating base formulation in a cassette-style format readily adaptable to several distinct classes of interfacial properties. The surface coating is engineered with the following components that permit facile, customized, tailoring of the platform chemistry across a number of applications: a non-specific binding matrix affixed upon and/or to the substrate; and an active component affixed to the non-specific binding matrix.

The active component 106 is preferably the same as is described above with respect to the method for producing a functional surface 100. The non-specific binding matrix facilitates adherence of the active component upon and/or to the substrate. Preferably, the non-specific binding matrix has a matrix-forming component and a cross-linking component. The matrix-forming component and the reactive component are identical to those described above with respect to the method for forming a functional, selective-binding surface. Coating adhesion upon and/or to the underlying substrate is believed to be promoted by multiple non-covalent interactions (e.g., physical entanglement, non-covalent binding) between the insoluble cross-linked film matrix and substrate in addition to any covalent linkages directly to the substrate via chemical reaction.

The surface chemistries of the present invention can be utilized in numerous analytical systems, including immunodiagnostics, gene and protein microarrays and microfluidic "lab-on-a-chip" devices. Application of the surface chemistries to these analytical settings are accomplished using the compositions and methods of the present invention in ways known to one of skill in the art. Example analytic assays for use with the present invention include, but not limited to, TMB-microwell assay, which is described in the following Examples, the staphylococcal enterotoxin B sandwich assay, also described in the following Examples, oligonucleotide microarray assays, also described in the following Examples, as well as other like capture assays that quantify the presence of antigens, pathogens, particles, drugs, toxins, and metabolites.

Note that different embodiments of the surface coating 100 of the present invention may be packaged together with a number of surface coating compatible, useful, target assay ingredients to provide kits appropriate for performing analytical assays. For example, kits may include a solution of prepared surface coating, target substrate, for example primed or un-primed glass slides, assay ingredients, for example, labeled antibody, and other helpful tools (pipettes, filters, tubes, etc). Note also that kits may be packaged with the substrate pre-coated with the target surface coating for use in the particular assay of interest.

Further, the surface chemistries of the present invention can be utilized within the medical device implant field to limit or eliminate non-specific binding to the implanted device, examples include coatings to surfaces of existing devices such as catheters, shunts, pumps, filtration membranes, stents, valves, membranes and other devices. Such coatings are commonly used to reduce non-specific adsorption of biological components, cells and microbes.

In another potential embodiment, the surface chemistries of the present invention can be utilized within the medical device implant field to provide coatings that provide active functions. For example, the surface chemistries of the present invention can be used to entrap drugs for controlled release applications. In another example, the surface chemistries of the present invention could be used to tether drugs, therapeutic proteins, antimicrobial compounds, etc. to the surface of a device.

Having generally described the invention, the same will be more readily understood by reference to the following examples, which are provided by way of illustration and are not intended as limiting.

EXAMPLE I

Low Non-Specific Binding (NSB) Biotinylated Surface Coating Chemistry on a $SiO_2$/Si Substrate The following example illustrates the utility of an embodiment of the present invention for limiting NSB of a protein to a treated $SiO_2$/Si substrate. A coating solution was prepared and used to form a low NSB, biotinylated, surface coating on a flat $SiO_2$/Si substrate. Experiments tested the level of non-specific binding to either an untreated $SiO_2$/Si substrate or to the low NSB, biotinylated, surface-coated $SiO_2$/Si substrate.

Coating Solution Preparation. An aminosilane solution in organic solvent was prepared in a polypropylene vial by adding 26.5 µl (3-trimethoxysilylpropyl)-diethylenetriamine (Gelest) to 10 ml of solvent. Either dimethyl sulfoxide (DMSO) or n,n-dimethylacetamide (DMAC) can be used as the solvent (both from Aldrich). 1.0 ml of this solution was then added to a 40 mg aliquot of biotin-PEG-$CO_2$—N-hydroxysuccinimidyl (Biotin-PEG-NHS, Shearwater Polymers, Inc.), where PEG is a 3400 molecular weight polyethylene glycol. The NHS group of the Biotin-PEG-NHS reacts with the terminal amine on the amino silane to form a biotin-PEG-silane molecule. The biotin-PEG-silane/DMAC solution will be referred to as solution A.

In a second vial, 70.6 µl of 6-azidosulfonylhexyl-triethoxysilane was added to 10 ml DMSO. 125 µl of matrix forming agent (polyoxyethylene sorbitan tetraoleate, PST, Aldrich) was then added to this solution yielding a solution B. Solutions A and B were combined in a 1:4 volume ratio (1 ml solution A added to 4 ml solution B) to give a final coating solution mixture used for spin coating onto target substrates.

Spin-Coating. 5-inch silicon wafers (p- or n-type, single-side polished, test grade wafers) were loaded in a spin coater (Laurell Technologies Corp.) and spun at 5000 rpm. The coating solution (0.5 ml) was dispensed onto the spinning wafer, and the wafer was allowed to spin for 90 seconds.

Coated silicon wafers were placed in a vacuum oven pumped down to a vacuum of 150 mm Hg (absolute) for 30 minutes. The oven was then turned on and allowed to heat to approximately 140° C. The total thermal treatment (heating ramp and hold) was for two hours. The wafers were then allowed to cool to room temperature in ambient air.

Six-millimeter diameter sample spots were defined on the wafer by stamping a silicone adhesive border pattern onto the surface. The wafer was then diced into square pieces as is well known in the art and used in various assays.

Non-Specific Protein Binding (NSB) Assay. The following assay is illustrative of the non-specific binding levels of a model soluble globular serum protein on the coating solution treated wafer surface. An immunoglobulin G (IgG) antibody (160 kDa) was used as the model non-specific binding protein. Specifically, a horseradish peroxidase conjugate of rabbit anti-sheep IgG (KPL Laboratories) was dissolved in phosphate buffered saline (PBS) to provide a series of IgG concentrations, ranging from 0.1 to 10 µg/ml. The sample to be assayed ("test piece") was first triple-rinsed with high purity water and blown dry with a stream of $N_2$ gas. 20 µl of varying concentrations of the IgG-PBS solution were placed on test spots and incubated at 37° C. in a 100% (nominal) humidity chamber for 30 minutes. Various IgG test concentrations were used as described below. After incubation, the test spots were again triple rinsed with high purity water and blown dry with $N_2$ gas. 20 µl droplets of a commercial tetramethylbenzidine (TMB) peroxidase substrate were then added to each test spot. Each test piece was incubated at 37° C. in a 100% (nominal) humidity chamber for 30 minutes.

HRP catalyzes the formation of an insoluble, surface-deposited membrane in this assay, which can be detected calorimetrically or by ellipsometry. As such, the greater the level of NSB of horseradish peroxidase coupled IgG to the test piece, the greater the level of surface-deposited membrane.

Control Experiments: Bare Substrates and BSA Blocking. In addition to the coating solution treated substrates discussed above, two NSB control experiments were also run in parallel: (1) bare $SiO_2$/Si wafer substrates; and (2) $SiO_2$/Si wafers blocked with bovine serum albumin (BSA). BSA-blocking is currently the most widely used technique for inhibiting non-specific protein binding on bioassay surfaces. Briefly, an untreated piece of silicon wafer was triple-rinsed in high purity water and blown dry with $N_2$ gas. 40 µl droplets of a 1% BSA solution in PBS were then placed on each 6 mm test spot. The droplet covered the entire test spot, which was then incubated for 1 hour at 37° C. and 100% (nominal) relative humidity. The BSA solution was then rinsed off with high purity water and blown dry with $N_2$ gas, and the NSB assay described above was performed on the BSA-blocked $SiO_2$/Si substrate.

Figure 2:
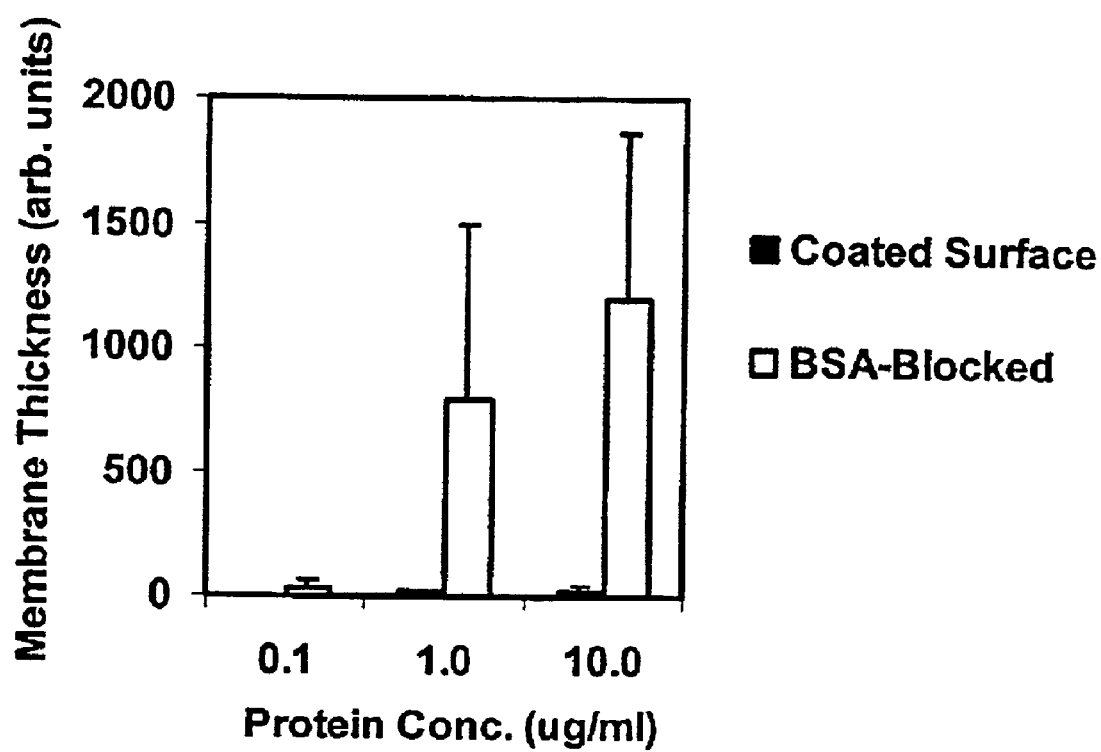
FIG. 2 illustrates the non-specific binding of protein on biotin functional surfaces in accordance with one embodiment of the present invention on $SiO_2/Si$ wafers, compared to BSA-blocked $SiO_2/Si$ wafers.

The data in FIG. 2 illustrates that coated or treated $SiO_2$/Si substrates of the present Example showed little or no detectable IgG non-specific binding at any of the tested concentrations (solid bars). In contrast, BSA-blocked wafers showed a much greater level of IgG NSB (open bars). Note the large error bars on the BSA-blocked surface data, indicating the IgG NSB variability commonly encountered with this blocking technique. NSB was very high on the bare $SiO_2$/Si wafers, and increased off-scale for the 1 and 10 µg/ml IgG protein loading (data not shown).

This data supports a conclusion that biotin functional surfaces of the present invention are effective at limiting or eliminating NSB of proteins to $SiO_2$/Si substrates. In contrast, bare $SiO_2$/Si, and to a lesser extent BSA-blocked $SiO_2$/Si substrates, showed a greater level of non-specific protein binding, illustrating again the effective utility of the present invention.

EXAMPLE II

Low Non-Specific Binding (NSB) Thiol-Reactive Surface Coating Chemistry on $SiO_2$/Si Substrates The following example illustrates the utility of another embodiment of the present invention for limiting NSB of a protein to a treated $SiO_2$/Si substrate. A coating solution was prepared and used to form a low NSB, thiol-reactive, surface coating on a $SiO_2$/Si substrate. Experiments were performed to test the level of non-specific binding to either an untreated $SiO_2$/Si substrate or to the low NSB, thiol-reactive, surface coated $SiO_2$/Si substrate.

Coating Solution Preparation. The coating solution was prepared as essentially described in Example I, with the exception that the Biotin-PEG-NHS was replaced with vinylsulfone-PEG-NHS (Shearwater). Spin coating was also performed as essentially described in Example I.

The spin coated wafers were placed in a vacuum oven pumped down to a vacuum of 150 mm Hg (absolute) for 30 minutes. The oven was then turned on and allowed to heat to approximately 70° C. The total thermal treatment (heating ramp and hold) was for four hours. The wafers were then allowed to cool to room temperature in ambient air.

Six-millimeter diameter sample spots were defined on the wafer by stamping a silicone adhesive border pattern onto the surface. The wafer was then diced and used in various binding assays.

Non-Specific Protein Binding (NSB) Assay. Non-specific protein binding was assessed using a soluble TMB-microwell assay. Briefly, as described in Example 1, each test piece was rinsed with high purity water, dried, and incubated with a solution of horseradish peroxidase conjugate of rabbit anti-sheep IgG. Note that the PBS solution in this Example included 0.1% Tween20 surfactant. After protein incubation and rinsing, 20 $\mu$l droplets of a commercial, tetramethylbenzidine (TMB) soluble peroxidase substrate solution were added to each test spot. 20 $\mu$l of stop solution was added to each TMB droplet after 30 minutes incubation at 37° C. and 100% (nominal) relative humidity. The stop solution stops the enzymatic reaction and locks in the color change in the droplet. Droplets were combined using a micropipet and 80 $\mu$l samples were transferred from the test piece to a microtiter plate. A plate reader monitoring optical density at 450 nm was used to quantify the extent of the peroxidase reaction, which is directly related to the quantity of non-specifically bound IgG-HRP to each test piece.

Control Experiments: Bare Substrates and BSA Blocking. In addition to the coating solution treated substrates discussed above, two NSB control experiments were also run in parallel: (1) bare $SiO_2$/Si wafer substrates; and (2) $SiO_2$/Si wafers blocked with bovine serum albumin (BSA). As discussed in Example I, BSA-blocking is currently the most widely used technique for inhibiting non-specific protein binding on bioassay surfaces. The BSA-blocking protocol was essentially as described in Example I. The test piece was triple-rinsed in high purity water and blown dry with $N_2$ gas. 40 $\mu$l droplets of a 1% BSA solution in PBS were then placed on each 6 mm test spot. The droplet covered the entire test spot, which was then incubated for 1 hour at room temperature and 100% (nominal) relative humidity. The BSA solution was then rinsed off with high purity water and blown dry with $N_2$ gas.

Figure 3:
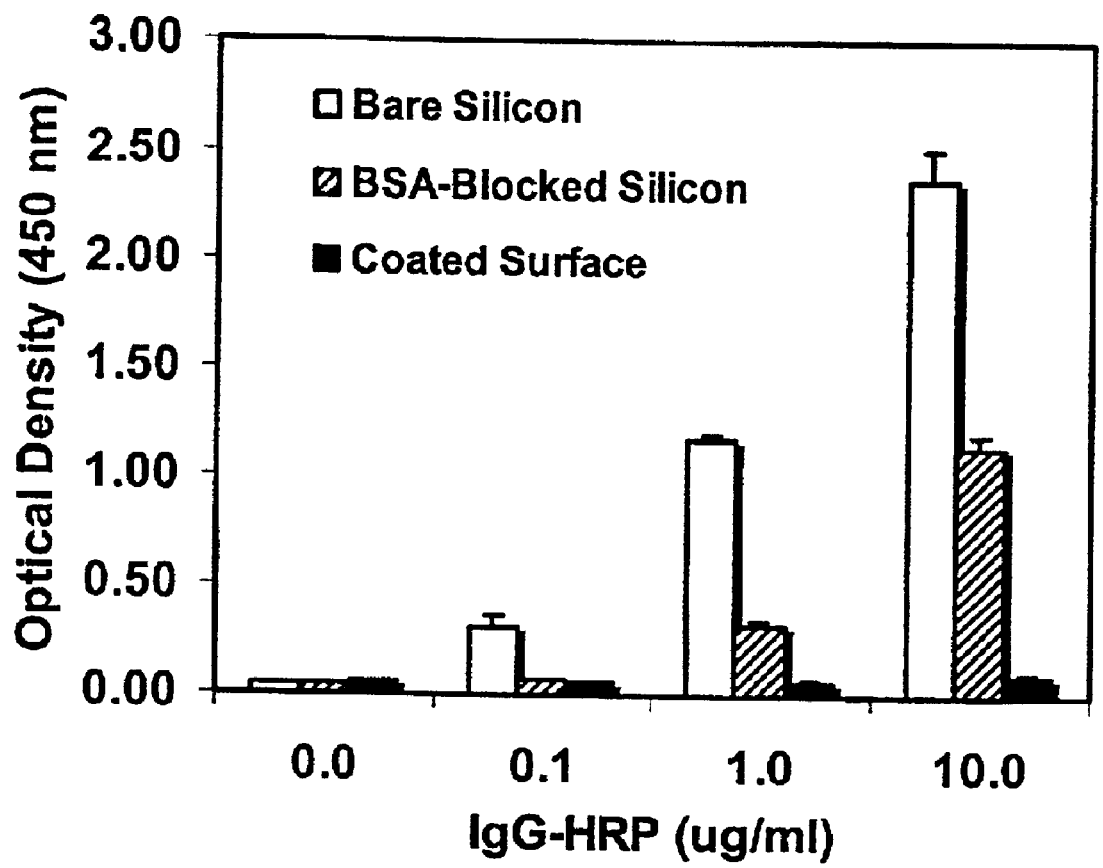
FIG. 3 illustrates the non-specific binding of protein on thiol-reactive functional surfaces in accordance with one embodiment of the present invention on $SiO_2/Si$ wafers, relative to BSA-blocked and bare $SiO_2/Si$ wafers.

NSB Results: The data in FIG. 3 illustrates that coated or treated $SiO_2$/Si substrates of the present Example showed little or no detectable IgG binding at any of the tested IgG concentrations (solid bars). In contrast, BSA-blocked wafers showed a much greater level of IgG NSB (cross-hatched bars). Note the large error bars on the BSA-blocked surface data, indicating the IgG NSB variability commonly encountered with this blocking technique. NSB was very high on the bare $SiO_2$/Si wafers (open bars), and increased off-scale for the 1 and 10 $\mu$g/ml IgG protein loading (data not shown).

This data supports a conclusion that thiol-reactive functional surfaces of the present invention are effective at limiting or eliminating NSB of proteins to $SiO_2$/Si substrates. In contrast, bare $SiO_2$/Si, and to a lesser extent BSA-blocked $SiO_2$/Si substrates, showed a greater level of non-specific protein binding, illustrating again the effective utility of the present invention.

EXAMPLE III

Low Non-Specific Binding (NSB) Biotinylated Surface Coating Chemistry on Plastic (Polymeric) Substrates The following example illustrates the utility of an embodiment of the present invention for limiting NSB of a protein to a plastic (polymeric) substrate. A coating solution was prepared and used to form a low NSB, biotinylated, surface coating on the plastic substrate, e.g., polystyrene, polysulfone, polyetherimide, and polyethersulfone. Experiments were performed to test the level of non-specific binding to either an untreated plastic substrate or to the low NSB, biotinylated, surface coated plastic substrate.

Polystyrene (PS). The polystyrene substrates consisted of 3-inch hydrophobic disks approximately 2 mm thick. The disks were cut from bacteriological grade polystyrene Petri dishes (VWR). The coating solution preparation was identical to that described in Example I. Prior to coating the polystyrene Petri dishes with the coating solution, an oxidation step was performed on the hydrophobic polystyrene surface. Oxidation of the surface was accomplished by submerging the disk in concentrated sulfuric acid (95% $H_2SO_4$, Mallinkrodt) for two minutes. The disks were then rinsed extensively with high purity water and blown dry with $N_2$ gas. The disk was mounted in the spin coater and spun at 5000 rpm. The coating solution (0.5 ml) was dispensed onto the spinning disk and was allowed to spin for 90 seconds. At that point another 0.5 ml of the coating solution was dispensed and spun for 90 seconds. The PS surface thus received two coats of coating solution during the spinning process.

The coated PS disk was then placed in a vacuum oven that was evacuated to 150 mm Hg (absolute) at room temperature for 30 minutes. After the 30-minute pump down, the oven was turned on and the samples were heated to 90° C. under vacuum. The total time for thermal treatment (heat ramp and hold) was four hours. Each sample was then allowed to cool to room temperature under ambient atmosphere. After cooling, 6 mm test spots were defined on the surface by stamping with a silicone adhesive border pattern.

Polysulfone (PSU), polyetherimide (PEI), and polyethersulfone (PES). These substrates consisted of 2-inch square coupons cut from 0.02-inch thick commercial film stock. The coupons were cleaned by sonicating for 15 minutes in a non-ionic detergent (Triton X-100) bath. After extensive high purity water rinsing, the coupons were sonicated for another 15 minutes in a 50:50 ethanol:water solution, followed by a water rinse and $N_2$ gas blow dry.

The coating solution preparation was essentially identical to that described in Example I. The coupons were mounted in the spin coater and spun at 5000 rpm. 0.3 ml of the coating solution was dispensed on the coupons and spun for 90 seconds. The coupons were then placed in a vacuum oven that was pumped down to a vacuum of 150 mm Hg (absolute) for 30 minutes. The oven was then turned on and allowed to heat to approximately 140° C. The total thermal treatment (heating ramp and hold) was for two hours. The coupons were then allowed to cool to room temperature in ambient air. Six-millimeter diameter sample spots were defined on the wafer by stamping a silicone glue on the surface.

Non-Specific Binding (NSB) Assay. Non-specific protein binding was assessed using a soluble TMB-microwell assay. First, coated PS, PSU, PEI or PES surfaces were rinsed and incubated with the horseradish peroxidase conjugate of rabbit anti-sheep IgG (described in Example 1), with the exception that the phosphate buffered saline also contained 0.1% Tween20 surfactant. After protein incubation and rinsing, 20 µl droplets of a commercial, tetramethylbenzidine (TMB) soluble peroxidase substrate solution was added to each test spot. 20 µl of stop solution was added to each TMB droplet after 30 minutes incubation at 37° C. and 100% (nominal) relative humidity. The stop solution stops the enzymatic reaction and locks in the color change in the droplet. Droplets were combined using a micropipet and 80 µl samples were transferred from the test piece to a microtiter plate. A plate reader monitoring optical density at 450 nm was used to quantify the extent of the peroxidase reaction, which is directly related to the quantity of non-specifically bound IgG-HRP to each surface.

Figure 4:
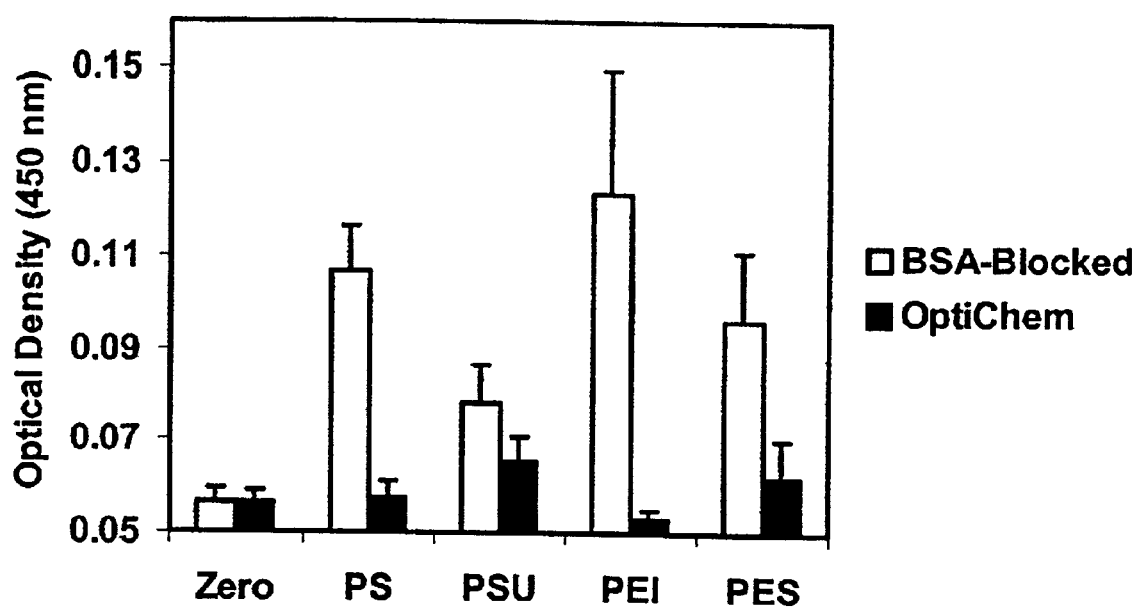
FIG. 4 illustrates the non-specific binding of protein on BSA-blocked substrates and functional surfaces according to one embodiment of the present invention on various plastic substrates.

NSB Results. FIG. 4 provides representative non-specific protein (IgG) binding results. The data presented compare the performance of our surface coating (solid bars) relative to traditional bovine serum albumin (BSA) blocking (open bars).

The data correspond to incubation in 10 µg/ml IgG for each of the plastic substrate (PS, PSU, PEI, PES), and show that our surface coating is more effective in inhibiting NSB than BSA-blocking on these widely used plastic substrates.

EXAMPLE IV

Low Non-Specific Binding (NSB) Biotinylated Surface Coating Chemistry on Metal/Metal Oxide Substrates The following example illustrates the utility of an embodiment of the present invention for limiting NSB of a protein to a metal/meal oxide substrate. A coating solution was prepared and used to form a low NSB, biotinylated, surface coating on the metal/metal oxide substrate. Experiments were performed to test the level of non-specific binding to either a BSA blocked metal/metal oxide substrate or to the low NSB, biotinylated, surface coated metal/metal oxide substrate.

The metal substrate consisted of a 30 nm gold film vapor deposited onto a 5-inch silicon wafer. A ~5 nm chromium adhesion interlayer was used between the gold and silicon oxide. The coating solution preparation was identical to that described in Example I. The gold-coated wafer was mounted in the spin coater and spun at 5000 rpm. 0.5 ml of the coating solution was dispensed onto the wafer that was spun for 90 seconds. A second application of 0.5 ml coating solution was dispensed onto wafer and spun for another 90 seconds. As such, the metal/metal oxide substrate surface received two coats of coating solution during the spinning process.

The coated wafer was then placed in a vacuum oven that was pumped down to a vacuum of 150 mm Hg (absolute) for 30 minutes. The oven was then turned on and allowed to heat to approximately 140° C. The total thermal treatment (heating ramp and hold) was for two hours. The wafers were then allowed to cool to room temperature in ambient air. Six-millimeter diameter sample spots were defined on the wafer by stamping silicone adhesive border pattern on the surface. Non-specific binding of protein was assessed using the soluble colorimetric TMB method as described in Example II.

Figure 5:
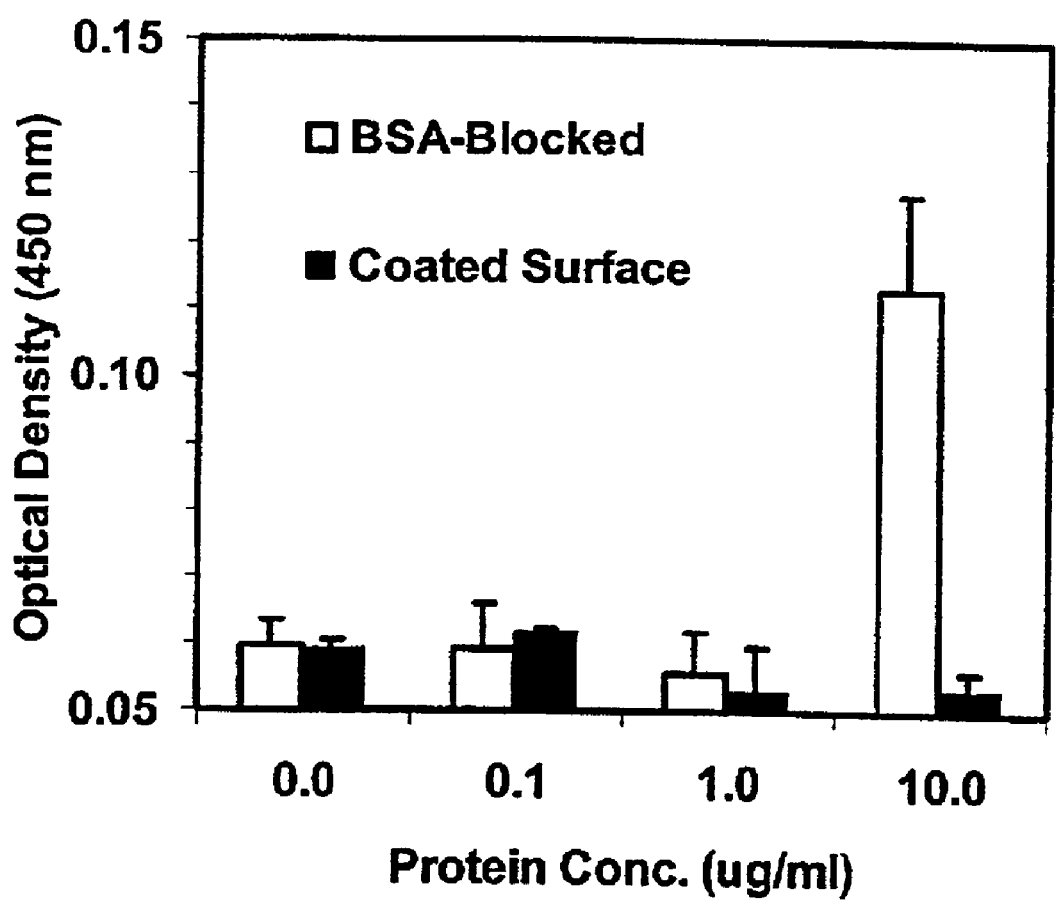
FIG. 5 illustrates the non-specific binding of protein on a BSA-blocked substrate and functional surfaces in accordance with one embodiment of the present invention on a metal substrate, in particular a gold substrate.

NSB Results: FIG. 5 provides representative non-specific protein (IgG) binding results. The data presented compare the performance of our surface coating relative to traditional bovine serum albumin (BSA) blocking. The data shows that the coated surface (solid bars) is superior to the traditional BSA-blocking approach (open bars) at an IgG protein solution load of 10 µg/ml. At lower protein concentrations, both surfaces are effective at inhibiting NSB.

This data supports a conclusion that biotinylated reactive functional surfaces of the present invention are effective at limiting or eliminating NSB of proteins to metal/metal oxide substrates. In contrast, BSA-blocked metal/metal oxide substrates, at 10 µg/ml or higher concentration, showed a greater level of non-specific protein binding, illustrating again the effective utility of the present invention.

EXAMPLE V

Low Non-Specific Binding (NSB) Thiol-Reactive Surface Coating Chemistry on Glass Microscope Slides The following example illustrates the utility of an embodiment of the present invention for limiting NSB of a protein to a glass microscope slide. A coating solution was prepared and used to form a low NSB, thiol-reactive, surface coating on the glass slide substrate. Experiments were performed to test the level of non-specific binding to either a bare glass slide, a BSA blocked glass slide or to the low NSB, thiol-reactive, surface coated glass slide.

Substrates (glass slides) used in this particular example were polished 25×75 mm microscope slides obtained from a commercial vendor (TeleChem SuperClean™) and used as received. Note, however, that several glass microscope slide substrates have been successfully used, including plain soda-lime glass slides.

Prior to coating, the slides were cleaned by the following protocol. First the slides were rinsed with high purity (18 MΩ-cm) water. Slides were then loaded in a glass staining rack, submerged in a 60° C., 1% Alconox solution (alkaline glass cleaner) and sonicated for 15 minutes. The slides were then rinsed with copious amounts of high purity water and sonicated in high purity water for another 15 minutes. Slides were then allowed to soak in fresh ultrapure water. Finally they were blown dry with $N_2$ gas. The slides were coated within two hours of cleaning.

Pre-primed glass slides have also been successfully coated. Primer coats include vapor deposited $SiO_2$ layers and spin-on glass formulations such as Seramic™ (Gelest).

The coating solution was prepared as described in Example II. Spin coating was performed as follows: a glass slide was mounted on the vacuum chuck of the spin coater. 0.5 ml of coating solution was dispensed on the stationary slide. The spinner was then turned on and accelerated to 3500 rpm, where it spun for 90 seconds.

The vacuum and thermal cure processes were identical to those described in Example H. The NSB assay and control experiments were performed as described in Example IV, with the following changes. After the 5 minutes TMB peroxidase substrate incubation, 20 µl of TMB-Stop solution was added to the test spots to stop the calorimetric reaction. Optical density was then read directly with the glass slide mounted on a 96-well plate holder (there was no fluid transfer to a microtitre plate).

Figure 6:
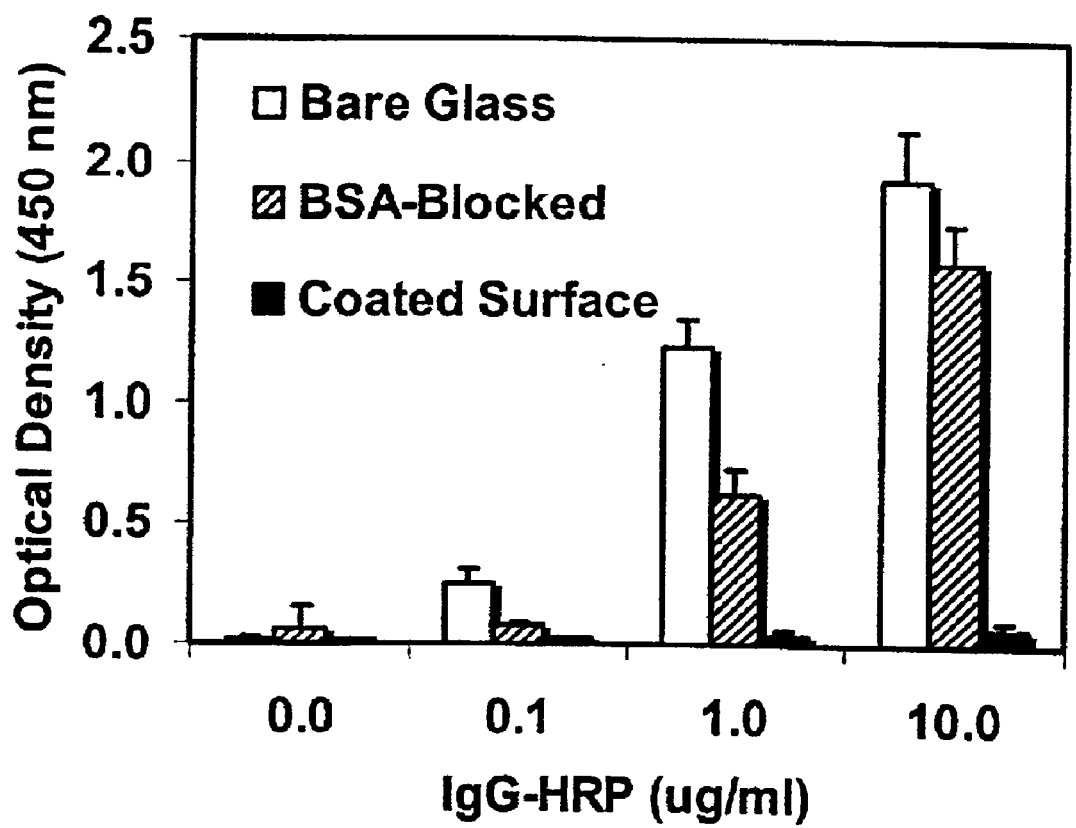
FIG. 6 illustrates the non-specific binding of protein on functional surfaces in accordance with one embodiment of the present invention on glass substrate, BSA-blocked glass, and bare glass substrate.

Binding Results: Results are presented in FIG. 6. These results show that the coated glass surface (solid bars) shows significantly lower non-specific protein binding than BSA-blocked (cross-hatched bars) and bare glass substrates (open bars).

This data supports a conclusion that thiol-reactive functional surfaces of the present invention are effective at limiting or eliminating NSB of proteins to a glass slide substrate. In contrast, bare glass sides and BSA-blocked glass slides showed a greater level of non-specific protein binding, illustrating again the effective utility of the present invention.

EXAMPLE VI

Low Non-Specific Binding (NSB) of Fibrinogen to Coated Surface

The following example illustrates the utility of an embodiment of the present invention for limiting NSB of fibrinogen to coated surfaces of the present invention. A coating solution was prepared and used to form a low NSB, thiol-reactive, surface coating on a $SiO_2/Si$ substrate. Experiments were performed to test the level of non-specific binding of fibrinogen to either a bare substrate, a BSA blocked substrate or to the low NSB, thiol-reactive, surface coated substrate.

Coated surfaces were prepared as described in Example II

Fibrinogen Non-Specific Protein Binding Assay. Non-specific fibrinogen binding was assessed using a soluble TMB-microwell assay as follows: test pieces were rinsed and test wells were incubated for 30 minutes with serial dilutions of human fibrinogen (Sigma) in phosphate buffered saline (PBS). After protein incubation, the substrates were rinsed three times with PBST (PBS with 0.01% Tween20) and one time with clean water and then blown dry. Each test well was then incubated for 30 minutes with a 20 µl droplet of a 1:8000 dilution of peroxidase labeled anti-human fibrinogen (Abcam) in PBST. The slides were rinsed as above and then 20 µl droplets of a commercial, tetramethylbenzidine (TMB) soluble peroxidase substrate solution. The TMB assay and optical density measurements were performed as described in Example IV.

Control Experiments: Bare Substrates and BSA Blocking. In addition to the coated substrates, two NSB control experiments were run in parallel, as essentially described in Example II.

Figure 7:
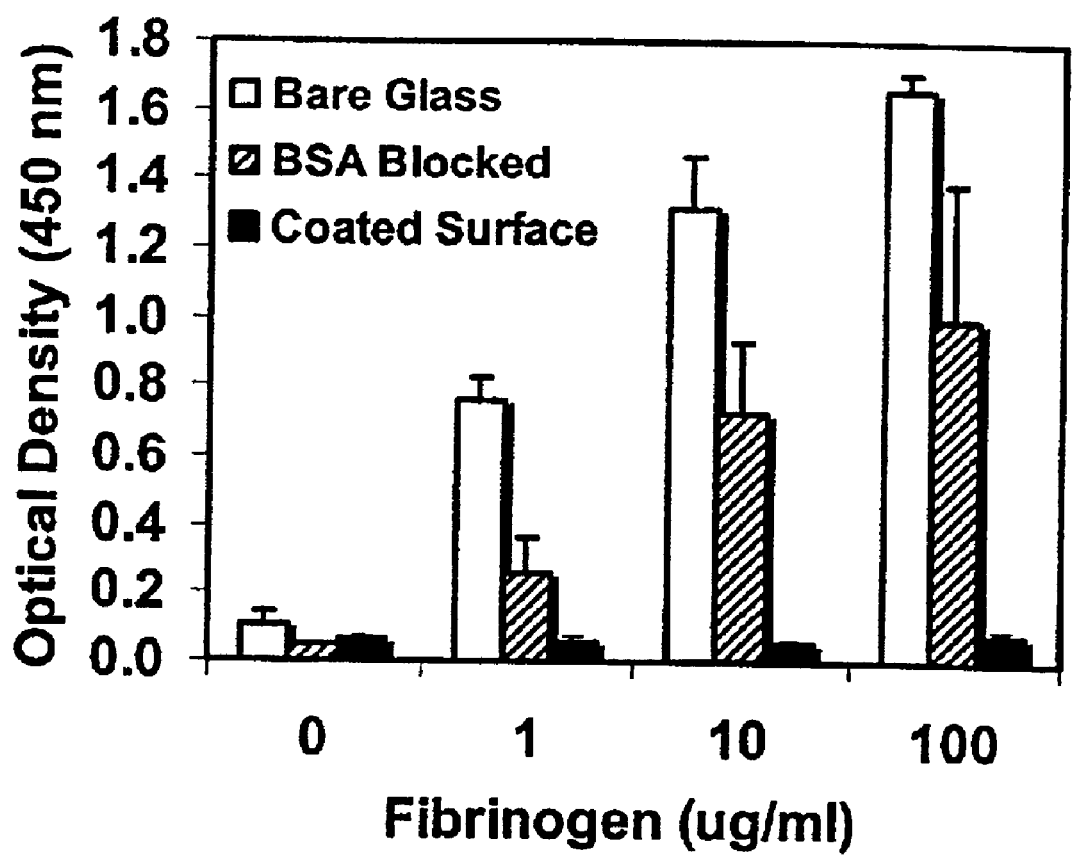
FIG. 7 illustrates the non-specific binding of fibrinogen on bare glass, BSA-blocked glass, and functional surfaces in accordance with one embodiment of the present invention.

NSB Results: Non-specific binding results are presented in FIG. 7. The coated surfaces (solid bars) show very low non-specific fibrinogen binding relative to the bare (open bars) and BSA-blocked (cross-hatched bars) surfaces.

This data supports a conclusion that thiol-reactive functional surfaces of the present invention are effective at limiting or eliminating NSB of fibrinogen to a target substrate. In contrast, non-treated substrate and BSA-blocked substrate showed a greater level of non-specific fibrinogen binding, illustrating again the effective utility of the present invention, especially in light of fibrinogens relative abundance as a serum protein.

EXAMPLE VII

Demonstration of Selective Versus Non-Specific Protein Binding on Coated Surfaces The following example illustrates the utility of an embodiment of the present invention for demonstrating selective protein (streptavidin) binding versus non-specific protein binding on biotinylated coatings. The test pieces in this study were film-coated silicon wafers, wherein the biotinylated coating was prepared as described in Example I. Control test pieces were also prepared as previously described except that control surfaces were prepared with non-reactive methoxy-capped PEG molecules instead of biotin. Specifically, these coatings were formed by replacing the biotin-PEG-NHS molecule in Example I with a methoxy-PEG-succinimidyl propionate (mPEG-SPA, MW 5000). Otherwise, all processing steps were identical to those in Example I.

Streptavidin binding to these surfaces was assessed using horseradish peroxidase conjugated streptavidin (SA-HRP, Pierce) and the soluble TMB-Microwell assay described in Example II. Various concentrations of SA-HRP were prepared in phosphate buffered saline with 0.01% Tween20 surfactant. 20 µl drops of SA-HRP solution were incubated on test spots for 30 minutes at 37° C. and 100% (nominal) relative humidity. The test spots were then rinsed with high purity water. The soluble TMB-microwell assay described in Example II was used to assess binding.

Figure 8:
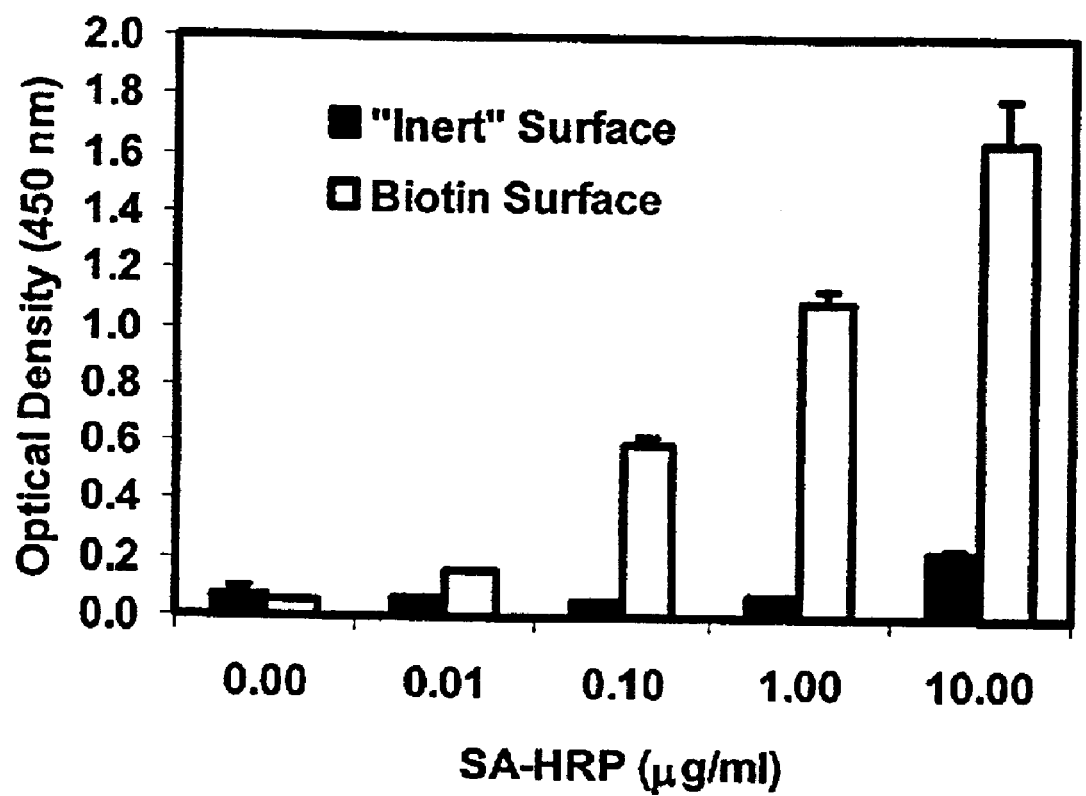
FIG. 8 illustrates the specific binding of streptavidin on biotin functional surfaces in accordance with one embodiment of the present invention.

Binding Results: FIG. 8 shows representative results. These results show that the biotinylated functional surface (open bars) binds significantly more streptavidin than the methoxy-PEG control surface ("inert" surface) (solid bars). Given the previous non-specific protein binding assay results (see Example I), we conclude that the SA is specifically bound to the biotinylated coating. The small signal observed on the methoxy-capped PEG sample for a SA load of 10 ug/ml is likely the result of a small amount of non-specific streptavidin binding.

This data supports a conclusion that functional surfaces of the present invention are effective at providing selective binding sites on a coated substrate, while inert functional surfaces of the present invention are effective at limiting non-specific binding on a coated surface.

EXAMPLE VIII

Demonstration of Biotinylated Molecule Binding to Streptavidin-Biotin Coated Surfaces The following example illustrates the utility of an embodiment of the present invention for demonstrating the fabrication of a streptavidin-biotin surface and the subsequent selective binding of a biotinylated molecules to this surface.

Coating Solution Preparation. A first aminosilane solution was prepared in a polypropylene vial by adding 26.5 µl (3-trimethoxysilylpropyl)-diethylenetriamine (Gelest) to 10 ml of N,N-dimethylacetamide (DMAC). 1.0 ml of this solution was then added to a 40 mg aliquot of biotin-PEG—$CO_2$—N-hydroxysuccinimidyl ester (Biotin-PEG-NHS, Shearwater Corp.), where PEG is a 3400 molecular weight polyethylene glycol. The NHS group reacts with the terminal amine on the amino silane to form a biotin-PEG-silane molecule. The biotin-PEG-silane/DMAC solution is called solution A. In a second vial, 70.6 µl of 6-azidosulfonylhexyl-triethoxysilane was added to 10 ml DMSO. 125 µl of matrix forming agent (polyoxyethylene sorbitan tetraoleate, PST, Aldrich) was then added to this solution, which is called solution B. Solution A and B were then combined in a 1:4 volume ratio (1 ml solution A added to 4 ml solution B) to give a final mixture called the biotin-PEG solution.

A second aminosilane solution was prepared in a polypropylene vial by adding 48.4 µl (3-trimethoxysilylpropyl)- diethylenetriamine (Gelest) to 10 ml of N,N-dimethylacetamide (DMAC). 1.0 ml of this solution was then added to a 40 mg aliquot of methoxy-PEG-succinimidyl propionate (mPEG-SPA, Shearwater Corp.), where PEG is a 2000 molecular weight polyethylene glycol. The NHS group reacts with the terminal amine on the amino silane to form a methoxy-PEG-silane molecule. The methoxy-PEG-silane/DMAC solution is called solution C. Solution C and B (described above) were then combined in a 1:4 volume ratio (1 ml solution A added to 4 ml solution B) to give a final mixture called the methoxy-PEG solution.

The biotin-PEG solution was then combined with the methoxy-PEG solution in a 1:4 volume ratio. This final mixture is used to coat a silicon substrate.

Spin-Coating. Spin-coating and the thermal cure were performed as described in Example I. Six-millimeter diameter sample spots were defined on the wafer by stamping a silicone adhesive border pattern onto the surface. The wafer was then diced and used in various assays.

Formation of the Streptavidin Layer. Streptavidin (Prozyme, Inc.) was diluted to 100 μg/ml in phosphate buffered saline (PBS). 40 μl droplets were then incubated in sample spots for one hour at room temperate. Several spots on the wafer were incubated with PBS only. These are the "no streptavidin" control spots. After incubation, the wafers were rinse three times with PBS-Tween20 (PBST) and one time with ultrapure water and were then blown dry. This process results in a streptavidin immobilized within the coating matrix.

Specific and Non-Specific Binding Assays. Biotinylated horseradish peroxidase (biotin-HRP, Pierce) was diluted to 10 μg/ml in PBST. 20 μl droplets were then incubated on test spots for 30 minutes at room temperature. Peroxidase labeled rabbit anti-sheep IgG (IgG-HRP) was used as a non-biotinylated control molecule. The IgG-HRP was diluted to 10 μg/ml in PBS (no Tween20), and 20 μl droplets were incubated on test spots for 30 minutes at room temperature.

Figure 9:
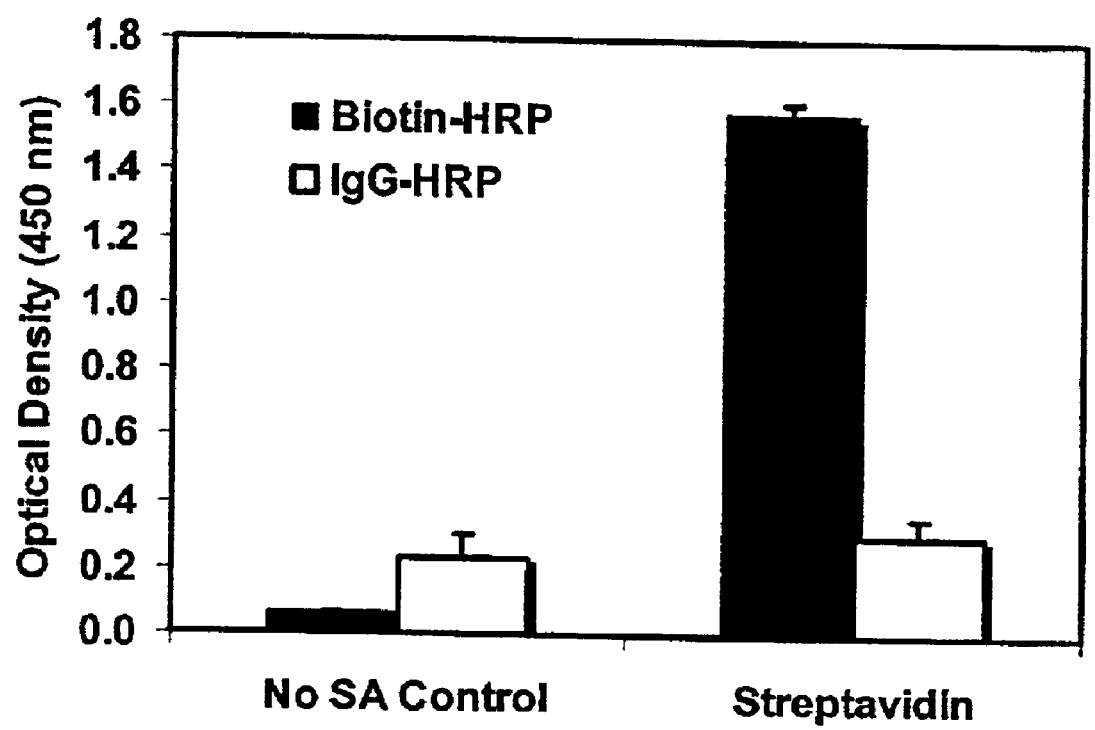
FIG. 9 illustrates the specific binding of biotinylated horseradish peroxidase to streptavidin functional surfaces in accordance with one embodiment of the present invention on glass substrates.

Results are presented in FIG. 9. The streptavidin-biotin surface shows significantly higher signal for biotin-HRP (solid bars) than for the non-biotinylated IgG-HRP (open bars). Relative to the streptavidin surface, neither biotin-HRP nor IgG-HRP show significant binding to the no-streptavidin control. The slightly higher signal for the IgG-HRP on the no-streptavidin surface can be attributed to the different incubation buffers. In the absence of Tween20 in the buffer, the IgG-HRP shows slightly higher non-specific binding.

This data supports a conclusion that biotinylated molecules specifically bind to streptavidin-biotin surfaces of the present invention, and conversely, that non-specific binding proteins show limited binding to these same coated surfaces. This Example again highlights the utility of the present invention.

EXAMPLE IX

Demonstration of Thiolated Protein Attachment to Thiol-Reactive Coatings on Polymer Substrates The following example illustrates the utility of an embodiment of the present invention for selectively attaching a thiolated protein on a thiol-reactive coating chemistry on a plastic substrate. Results are compared to binding of the thiolated protein to an inert control surface chemistry on a plastic substrate.

Coating Preparation. The coating solution was prepared as described in Example I, with the exception that the Biotin-PEG-NHS was replaced with vinylsulfone-PEG-NHS (Shearwater). Spin coating on tissue culture polystyrene (TCPS) was performed as described in Example III.

The coated wafer was then placed in a vacuum oven and was subsequently pumped down to a vacuum of 150 mm Hg (absolute) for 30 minutes. The oven was then turned on and allowed to heat to approximately 70° C. The total thermal treatment (heating ramp and hold) was four hours. The substrates were then allowed to cool to room temperature in ambient air. Six-millimeter diameter sample spots were defined on the surfaces by stamping a silicone adhesive border pattern onto the surface.

Inert Coating Preparation. The inert control surfaces were prepared exactly as described in Example VII.

The specific binding assays were performed at room temperature as follows: surfaces were first triple-rinsed with ultrapure (18 MΩ-cm) $H_2O$ and then blown dry with $N_2$ gas. Each test spot was then incubated with a 20 μl droplet of thiolated streptavidin in borate buffer (50 mM borate, 1 mM EDTA, pH 9.0, 0.01% Tween20). Incubation was at room temperature for 30 minutes. Note that no blocking step was used. After incubation, surfaces were triple-rinsed with PBST (0.1 M sodium phosphate, 0.15 M sodium chloride, pH 7.2, 0.01% Tween20) and blown dry. Test spots were incubated with a 1:100 dilution of biotin horseradish peroxidase (Pierce) for 30 minutes, rinsed with PBST, and then blown dry. Test spots were then incubated with a 20 μl droplet of TMB substrate. The enzyme catalyzed calorimetric TMB reaction was allowed to proceed for 5 minutes at which point it was stopped by applying a 20 μl droplet of stop solution. Optical density at 450 nm was read using a standard plate reader.

Figure 10:
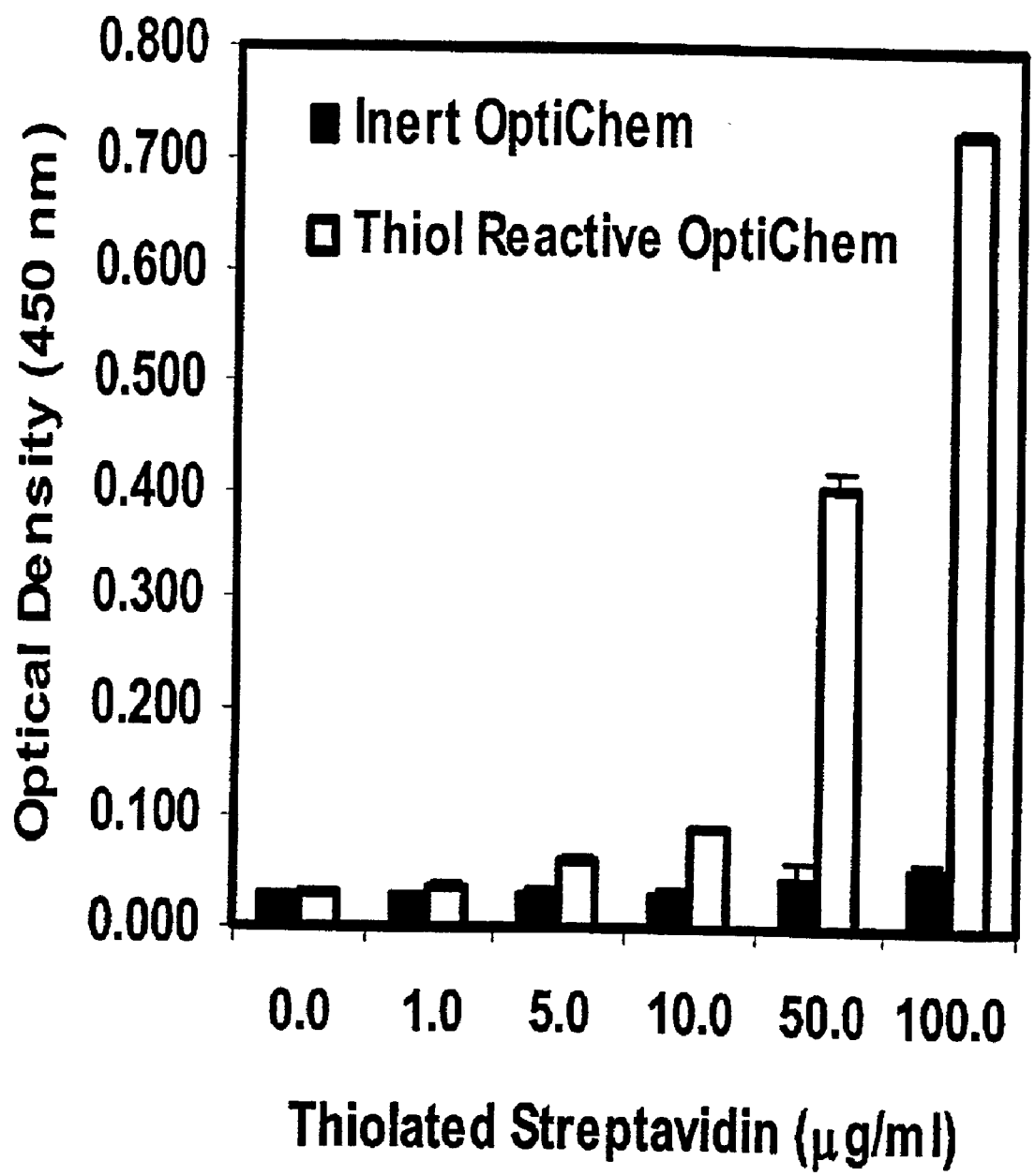
FIG. 10 illustrates the specific binding of thiolated streptavidin to thiol-reactive functional surfaces in accordance with one embodiment of the present invention on plastic substrates. Each concentration was run in triplicate and error bars represent one standard deviation in the set.

Binding Results: Specific binding results for the coated tissue culture polystyrene substrate are presented in FIG. 10 (note that each concentration was run in triplicate and error bars represent one standard deviation in the set). Binding of thiolated streptavidin to thiol-reactive coatings has been demonstrated (open bars). The dose response on the thiol-reactive coatings scales with concentration of thiolated streptavidin. Peroxidase activity on the inert surface is minimal (solid bars). The lack of non-specific binding on the inert surfaces provides solid evidence of covalent attachment of streptavidin to the thiol-reactive coatings.

EXAMPLE X

Demonstration of Protein Attachment to Amine-Reactive Coatings on Glass Microscope Slides The following example illustrates the utility of an embodiment of the present invention for selectively attaching an amine-containing protein to the amine-reactive coating chemistry, compared to a deactivated control surface, on glass microscope slides.

Coating Preparation. The coating solution was prepared as described in Example I, with the exception that the Biotin-PEG-NHS was replaced with a 80 mg aliquot of SPA-PEG-SPA (Shearwater) where SPA is a succinimidyl derivative of propionic acid that exhibits reactivity towards amine groups. Glass substrates in a 25×75 mm microscope slide format were primed with an approximate 400 angstrom RF sputtered silicon oxide layer and then cleaned by the following protocol. The slides were first rinsed with high purity (18 MW-cm) water to remove gross impurities. They were then loaded in a glass staining rack, submerged in an outgassed solution of 1% Alconox solution heated to 60° C. (alkaline glass cleaner) and sonicated for 15 minutes. The slides were then rinsed with copious amounts of high purity water and then sonicated in high purity water heated to 60° C. for another 15 minutes. The slides were then rinsed with copious amounts of high purity water and then placed in fresh high purity water until the drying step. Slides were exhaustively blown dry with compressed $N_2$ gas and were stored dry until use. The cleaned and primed slides were mounted in the spin coater and spun at 3500 rpm. 0.5 ml of the coating solution was dispensed onto the primed glass slide and spun for 90 seconds.

The coated 25×75 mm glass slide was then placed in a vacuum oven and was subsequently pumped down to a vacuum of 150 mm Hg (absolute) for 30 minutes. The oven was then turned on and allowed to heat to approximately 70° C. The total thermal treatment (heating ramp and hold) was 1 hour. The substrates were then allowed to cool to room temperature in ambient air. Six-millimeter diameter sample spots were defined on the surfaces by stamping a silicone adhesive border pattern onto the surface.

Specific Binding Assay: The specific binding assays were performed at room temperature as follows. Surfaces were first triple-rinsed with ultrapure (18 MΩ-cm) $H_2O$ and then blown dry with $N_2$ gas. An inert control surface was generated by chemically deactivating an amine-reactive coating using a 50 mM ethanolamine in a 50 mM borate buffer, pH 9.0 for 1 hour. Each test spot was then incubated with a 20 µl droplet of streptavidin in 50 mM phosphate buffer at pH 7.0. Incubation was at room temperature for 60 minutes. No blocking step was used. After incubation, surfaces were triple-rinsed with PBST (0.1 M sodium phosphate, 0.15 M sodium chloride, pH 7.2, 0.01% Tween20) and blown dry. Test spots were incubated with a 1:100 dilution of biotin horseradish peroxidase (Pierce) for 30 minutes, rinsed with PBS (0.1 M sodium phosphate, 0.15 M sodium chloride, pH 7.2), and then blown dry. Test spots were then incubated with a 20 µl droplet of TMB substrate. The enzyme catalyzed colorimetric TMB reaction was allowed to proceed for 5 minutes at which point it was stopped by applying a 20 µl droplet of stop solution. Optical density at 450 nm was read using a standard plate reader.

Figure 11:
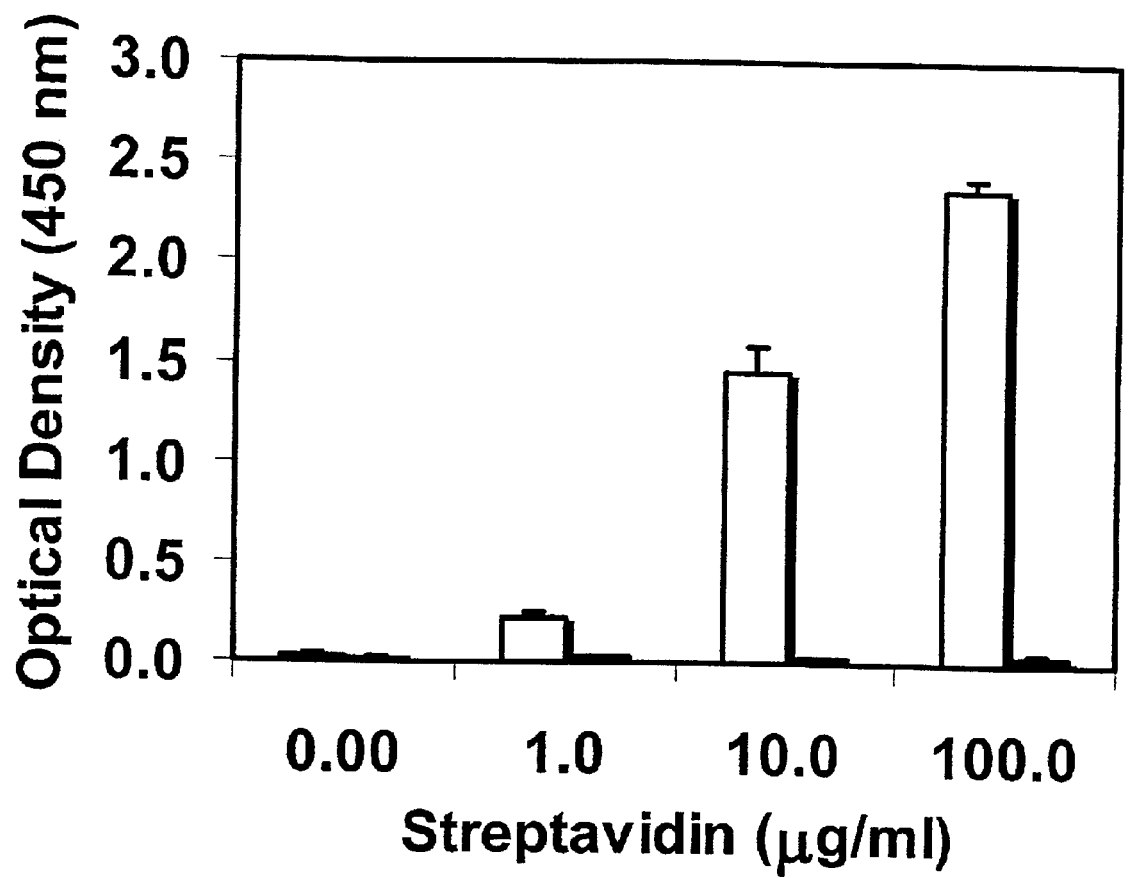
FIG. 11 illustrates the specific binding of streptavidin to amine-reactive functional surfaces in accordance with one embodiment of the present invention on primed glass substrates. Each concentration was run in triplicate and error bars represent one standard deviation.

Binding Results: Specific binding results for the amine-reactive coating are presented in FIG. 11. Streptavidin immobilization to the amine-reactive coatings has been demonstrated (open bars). The dose response on the amine-reactive coatings scales with concentration of streptavidin. Peroxidase activity on the deactivated surface is minimal (solid bars). The lack of non-specific binding on the deactivated coatings provides solid evidence for the covalent attachment of streptavidin to the amine-reactive coatings.

EXAMPLE XI

Demonstration of Selective Binding of Biotinylated Antibody to Streptavidin Coated Surfaces The following example illustrates the utility of an embodiment of the present invention for demonstrating the selective binding of a biotinylated antibody to a coated surface of the present invention.

Surface Fabrication. Glass microscope slides with amine reactive surface chemistries were prepared as described in Example X. Six-millimeter diameter sample spots were defined on the wafer by stamping a silicone adhesive border pattern onto the surface. Streptavidin was covalently attached through its surface amine using the following procedure. Streptavidin (Prozyme, Inc.) was diluted to 100 µg/ml in phosphate buffer (50 mM sodium phosphate, pH 7.0). 40 µl droplets of this solution were then incubated in sample spots for one hour at room temperate. The slides were then rinsed and the submerged in a deactivation solution consisting of 50 mM ethanolamine in 50 mM phosphate buffer, pH 7. The deactivation was allowed to proceed for 1 hour, at which point the slides were removed from the solution, rinsed with water and dried.

Assay. A biotinylated goat antibody (goat anti-mouse IgG, biotin-labeled, Pierce) was used as the positive sample. The control was a non-biotinylated goat antibody (goat anti-human myoglobin, ICN). Both antibodies were diluted to 100 µg/ml in phosphate buffered saline containing 0.005% Tween20 (PBST). 20 µl droplets of each antibody solution were incubated in sample spots for 30 minutes at room temperate. Several control spots were incubated with PBST only (no antibody). Slides were then rinse three times with PBST, one time with ultrapure water, and then dried. Goat antibody immobilized on the surface was assessed using immunochemistry. Specifically, 20 µl droplets of a peroxidase labeled anti-goat antibody (rabbit anti-goat IgG-HRP, KPL Inc., 1:100 dilution in PBST) were incubated on all test spots for 30 minutes at room temperature. The slides were then rinsed as above and incubated with 20 µl droplets of peroxidase substrate (TMB, KPL Inc.) for 5 minutes, at which point the colorimetric reaction was stopped with a TMB stop solution. Droplets were transferred to a 96-well microtitre plate and optical density at 450 nm was measured using a plate reader (Opsys MR, Thermo Labsystems).

Figure 12:
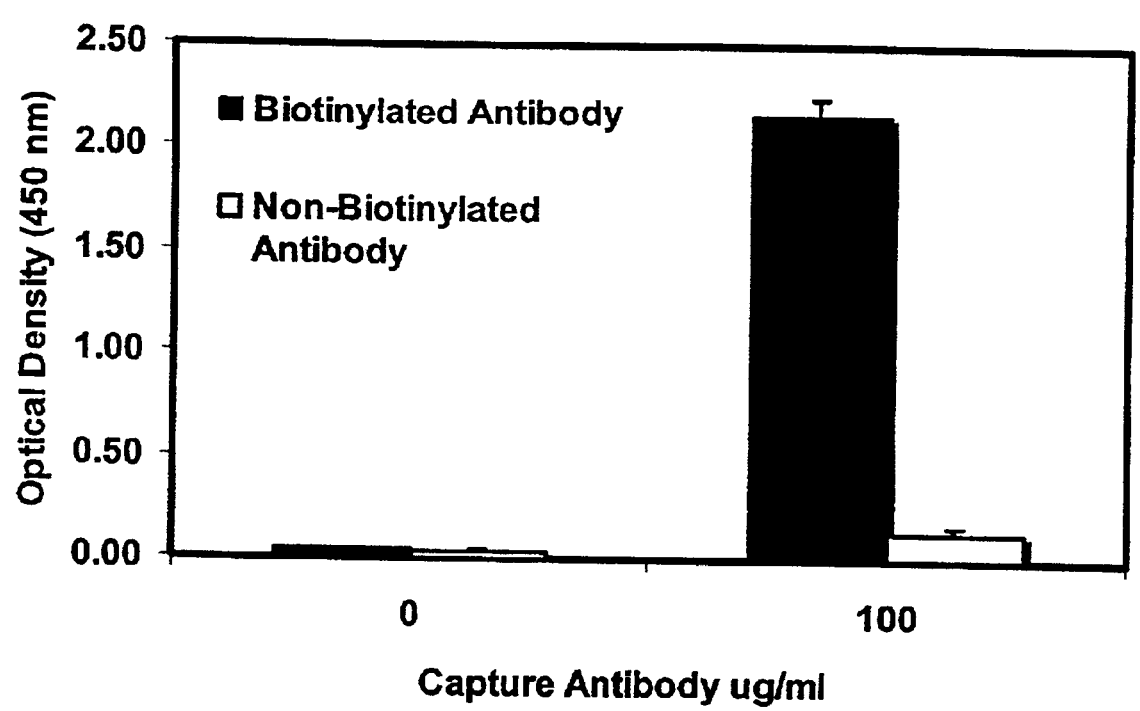
FIG. 12 illustrates the specific binding of biotinylated antibody to a streptavidin functional surface in accordance with one embodiment of the present invention on glass substrate.

Binding Results: Results are presented in FIG. 12. The data illustrates that in the absence of the first layer capture antibody (capture antibody concentration=0), the non-specific binding of the detection antibody (anti-goat, HRP) is very low (open bars). On surfaces incubated with the goat antibodies, results show that only the biotinylated antibody gives significant signal (solid bars). These results demonstrate that the surface embodiments of the present invention are selective for biotinylated antibody.

EXAMPLE XII

Demonstration of Improved Immunoassay Performance on Coated Surfaces

The following example illustrates the utility of an embodiment of the present invention by comparing the assay performance and detection limits of the coating chemistries of the present invention relative to a standard diagnostic assay. The comparison is based on sandwich enzyme-linked immunosorbent assay (ELISA) for staphylococcal enterotoxin B (SEB).

SEB Sandwich Assay Protocol for Coated Substrates. The substrates for this assay consisted of $SiO_2$/Si wafers coated with biotinylated, low-NSB surface coating as described in Example I. Streptavidin was bound to the surface by incubating 25 mg/ml (streptavidin in PBST) droplets (20 µl) at each 6 mm test spot. Incubation was for 30 minutes at 37° C. Each test piece was then triple-rinsed with high purity (18 MΩ-cm) water and blown dry with $N_2$ gas. Capture antibody was bound to each test spot by incubating with 20 µl droplets of biotin anti-SEB (Toxin Technologies). Incubation was performed for 30 minutes at 37° C. followed by a triple rinse in high purity water and the $N_2$ gas drying step. Test spots were then incubated with 20 µl droplets of the SEB antigen solution in concentrations ranging from 0.01 ng/ml to 1.0 ng/ml. Incubation was again performed for 30 minutes at 37° C. Test pieces were then triple rinsed with high purity water and blown dry. Detection antibody (anti SEB-HRP in PBST, 20 µl droplets, Toxin Technologies) was then incubated for 30 minutes at 37° C., followed by a triple rinsing with high purity water and blow dry. The final incubation was with a commercial, precipitate TMB assay. TMB-Membrane substrate (KPL, Inc.) was added in 20 µl droplets to each of the test spots and incubated for 30 minutes at 37° C. As described previously, HRP catalyzes the formation of an insoluble deposit on the surface. After blowing the test piece dry with $N_2$, the thickness of the deposited layer was quantified using a custom-built ellipsometer, providing an indirect, quantitative measurement of antigen at the surface.

SEB Sandwich ELISA Protocol. A standard ELISA format assay was performed for comparison to the SEB sandwich assay for coated surfaces discussed above. Briefly, 100 µl of capture antibody (biotin anti-SEB, Toxin Technology) in PBS-Tween (0.01%) was added to the wells of a 96-well microtiter plate (Dynex Technologies, Immulon 2HB) and was incubated for 120 minutes at 37° C. The wells were then triple rinsed with PBS solution, tapping fluid from the plate after each rinse. The wells were then blocked with bovine serum albumin (BSA) by adding 200 µl of 1% BSA in PBST and then incubating at 37° C. for 1 hour. SEB antigen solutions (Toxin Technology, 100 µl volumes with concentrations ranging from 0.01 ng/ml to 1.0 ng/ml in PBST) were added to the microwells and incubated at 37° for 60 minutes. The wells were then rinsed with PBST and fluid was tapped from the inverted plate. The detection antibody was a horseradish peroxidase conjugated anti-SEB (Toxin Technology). 100 ml volumes were incubated in each of the wells for 60 minutes at 37° C. Again, the wells were washed with PBST. Color was developed in the well by adding a commercial TMB peroxidase substrate (TMB-Microwell, KPL, Inc.). 100 µl volumes of the developer were added to the wells and were incubated for 60 minutes at 37° C. After 60 minutes, 100 ml of the TMB stop solution was added to each well, and the optical density at 450 nm was read using a microplate reader.

Figure 13A:
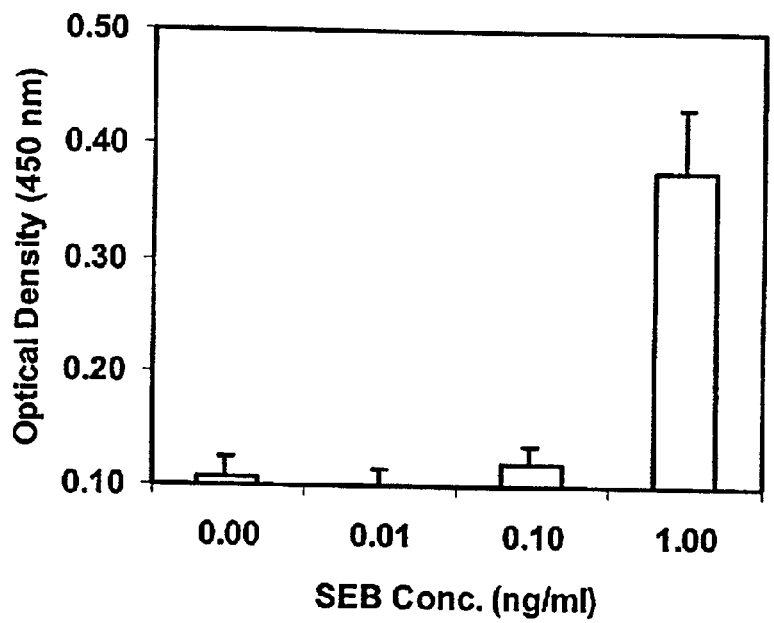
FIGS. 13(a) and (b) illustrate the improved assay sensitivity for staphylococcal enterotoxin B for a functional surface according to one embodiment of the present invention. Note that FIG. 13(a) shows optical density at 450 nm
Figure 13B:
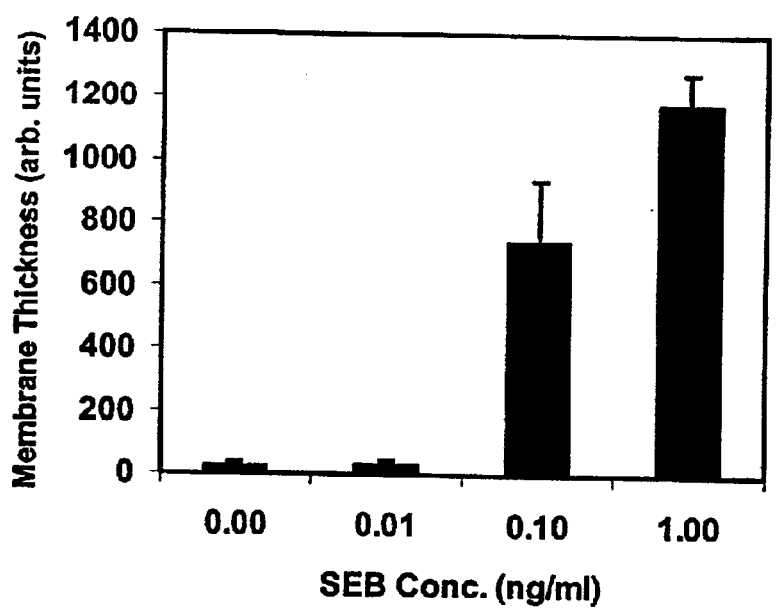
FIG. 13(b) shows membrane thickness.

Binding Results. Representative assay results are presented in FIG. 13(a), results of the standard microtiter plate ELISA assay, and FIG. 13(b), results for the ELISA assay performed on the functional coated surface of this invention. The important observation is that the coated surface, which presents specifically bound streptavidin for the sandwich assay, enables an order of magnitude improvement in assay sensitivity relative to a traditional sandwich ELISA. Specifically, the lower detection limit in the microtiter plate ELISA was approximately 1.0 ng/ml SEB. On the coated surface of the present invention, the lower detection limit was 0.1 ng/ml SEB.

EXAMPLE XIII

Surface Chemistry Comparison in Oligonucleotide Microarray Format

The following example illustrates the utility of an embodiment of the present invention as coating chemistries for use in oligonucleotide microassay formats. The experiments described in this example evaluate one coating chemistry embodiment of the present invention in parallel with current "state-of-the-art" commercial polymer and silane chemistries. In particular, the signal, noise and signal-to-noise levels are compared for the chemistries in a microarray format using amine labeled oligonucleotides.

Coating Preparation: The coating chemistry was prepared exactly as described in Example X The current state of the art commercial polymer chemistry is advertised as a three dimensional polymer coating on a glass slide substrate with a high loading capacity for amine labeled oligonucleotide. The commercial silane chemistry is advertised as a low background silane coating on a glass slide substrate. The commercial chemistries were processed according to the manufacturer suggested protocols, which are known and uniform for these types of substrates (two such manufacturers include:

Microarray Printing: 5' amine-linked and 3' biotin-labeled oligonucleotide (Operon) was suspended in 300 mM sodium phosphate buffer, pH 8.5 at a concentration of 20 µM. The coating chemistry was first triple-rinsed with ultrapure (18 MΩ-cm) $H_2O$ and then blown dry with $N_2$ gas prior to arraying. Commercial chemistries were used out of the box. An array of spots was printed on the chemistries using a SpotBot microarrayer (Telechem) fitted with SMP3B pins (Telechem). Commercial polymer and coating chemistries were incubated at 75% relative humidity for 5 hours. The polymer, silane and coating chemistries were stored desiccated at room temperature for 72 hours prior to use. The coating chemistry was deactivated with 50 mM ethanolamine in phosphate buffer pH 7.0 for 1 hour.

Specific Binding Assay: The commercial polymer chemistry was deactivated with a 50 mM ethanolamine in 0.1M Tris, pH 9.0, 1% SDS solution at 50° C. for 20 minutes. The commercial silane chemistry was baked at 80° C. for 2 hours then blocked with bovine serum albumin for 1 hour. The specific binding assays were performed at room temperature as follows: chemistries were incubated with 140 µl of 10 µg/ml of Cy5 labeled streptavidin (Amersham) in PBST (0.1 M sodium phosphate, 0.15 M sodium chloride, pH 7.2, 0.01% Tween20). 40 mm Lifter Slips (Erie) were utilized to spread liquid evenly over surface of slide chemistries. Chemistries were placed in hybridization chamber for 30 minutes. Lifter Slips were removed from slide chemistries and slides were triple-rinsed with PBST then ultrapure (18 MΩ-cm) $H_2O$ and dried. Slide chemistries were placed in GenePix 4000B scanner (Axon) and settings were optimized for the commercial polymer slide chemistry. Final scanner settings were 100% laser power and 500 volt setting on the photo multiplier tube.

Figure 14A:
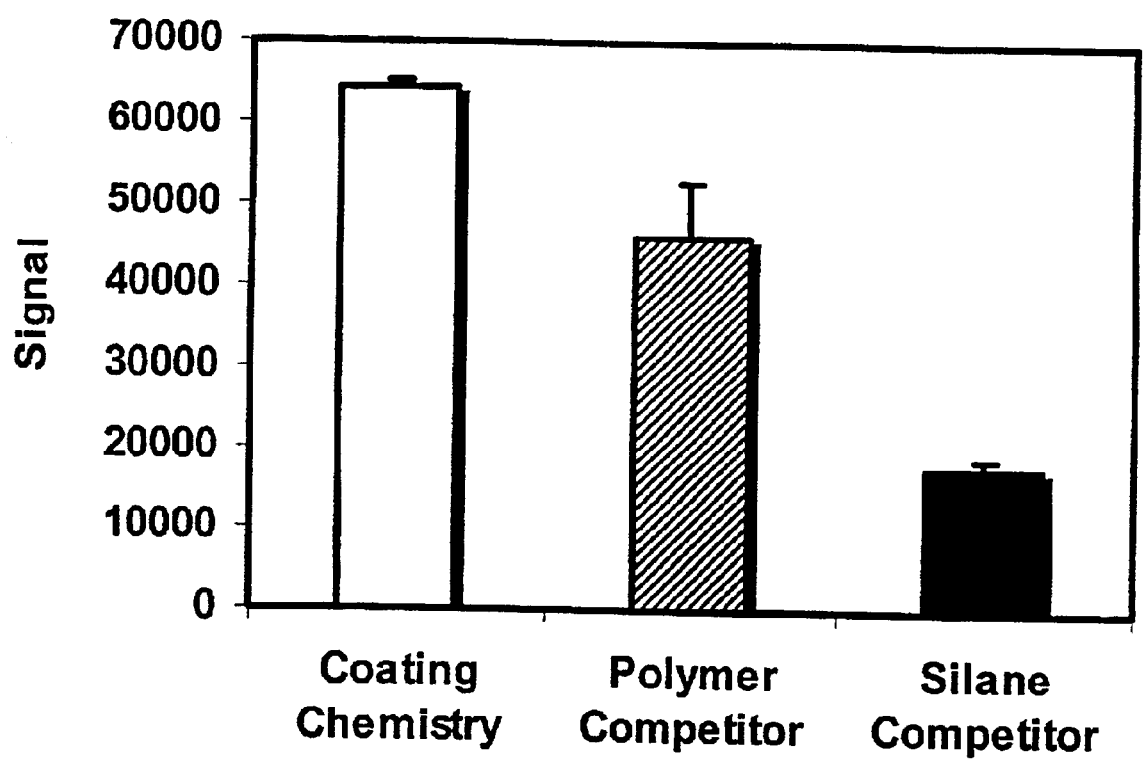
FIGS. 14(a), (b) and (c) illustrate the use of one embodiment of the present invention in an oligonucleotide microarray application, and specifically illustrates the use of oligonucleotides with amine-reactive functional surfaces in comparison to state-of-the-art commercial polymer and silane chemistries.

Binding Results: Specific binding results for the coating chemistry and commercial chemistries are presented in FIG. 14(a). Signal intensities are reported in relative fluorescence units. FIG. 14(a) shows that the coating chemistry (open bar) has higher signal intensity than both the polymer (cross-hatched bar) and silane (solid bar) chemistries in this experiment.

Figure 14B:
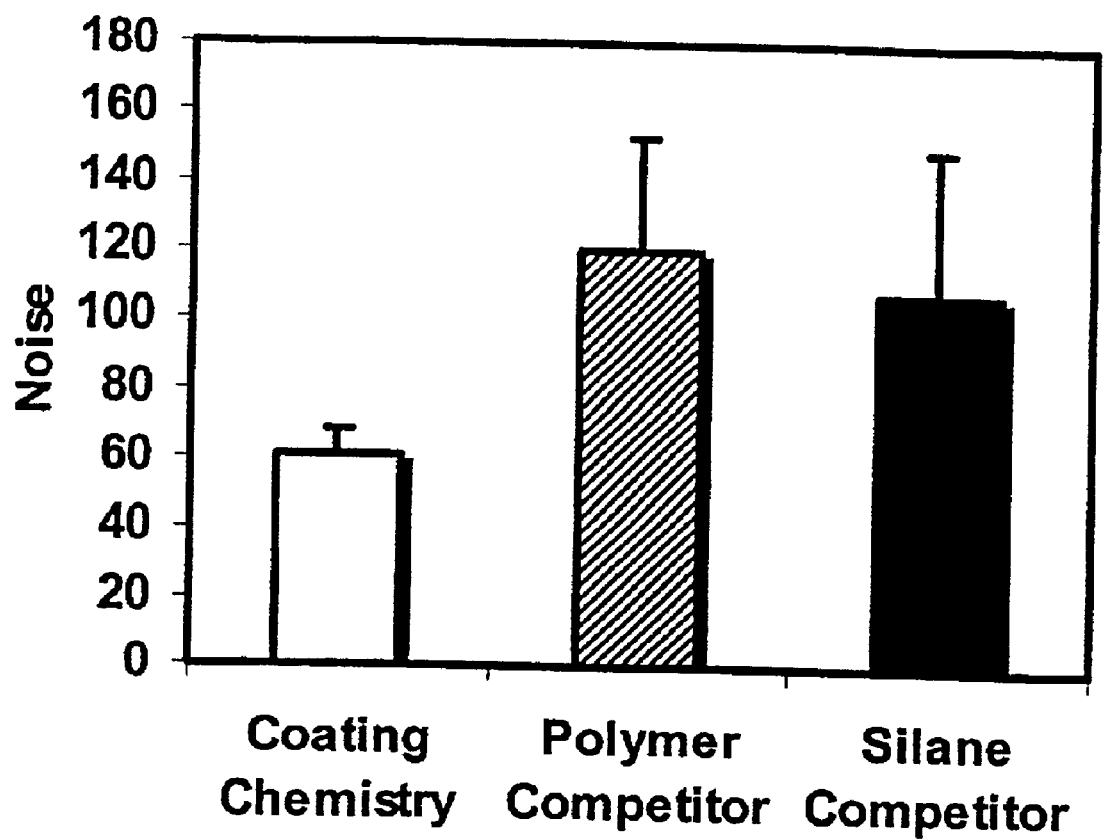
FIG. 14(b) shows fluorescence background determination where noise levels are reported in relative fluorescence units. Data obtained from one slide and error bars represent one standard deviation.

The background was monitored in the Cy5 channel. Noise levels are reported in relative fluorescence units. Representative non-spotted areas of the scanned image were used to calculate global background values. The Cy5 channel signal provides a measurement of the non-specific binding contribution to background signal. FIG. 14(b) shows the coating chemistry (open bar) has significantly lower Cy5 background compared to polymer (cross-hatched bar) and silane (solid bar) chemistries. The coating chemistry has lower background signal due to low surface non-specific binding of the Cy5 streptavidin.

Figure 14C:
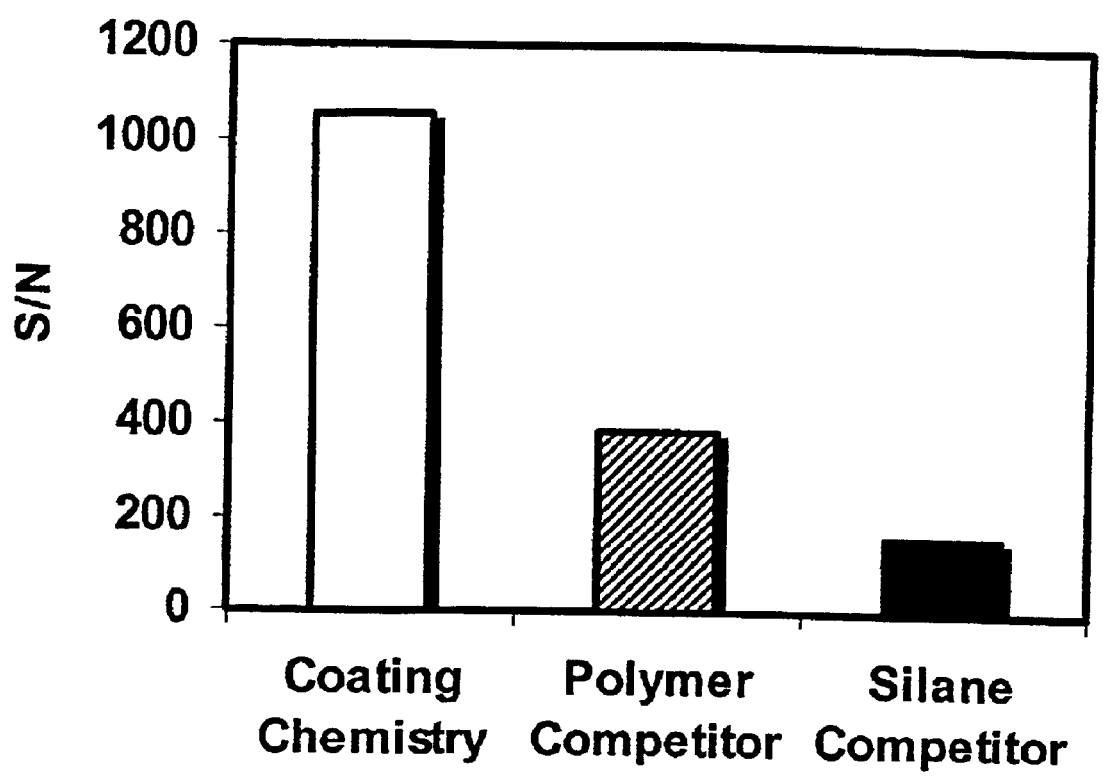
FIG. 14(c) shows the resulting signal-to-noise ratios (S/N) for the coating chemistry compared to the polymer and silane slide chemistries. One slide represented per data points.

Resulting signal-to-noise ratios in the Cy5 channel were calculated for the slide chemistries and are shown in FIG. 14(c). The coating chemistry (open bar) shows approximately 3× higher signal-to-noise ratio than the commercial polymer chemistry (cross-hatched bar) and a 6× improvement in signal-to-noise over the commercial silane chemistry (solid bar).

EXAMPLE XIV

Demonstration of Antibody-Antibody Interaction in a Protein Microarray

The following example illustrates the utility of an embodiment of the present invention for demonstrating the fabrication of an array of biotinylated antibodies on a coated surface of the present invention, and their subsequent detection using antibody-antibody recognition.

Surface Fabrication. Glass microscope slides with amine reactive surface chemistries were prepared as described in Example X. Streptavidin was covalently attached to the surface using the following procedure. First, an adhesive hybridization chamber (Schleicher and Schuell) was placed on the glass substrate. Streptavidin (Prozyme, Inc.) was diluted to 100 µg/ml in phosphate buffer (50 mM sodium phosphate, pH 7.0), and approximately 700 µl was added to the hybridization chamber, where the reaction was allowed to proceed for 1 hour. The chamber was then removed, and slides were rinsed and then submerged in a deactivation solution consisting of 50 mM ethanolamine in 50 mM phosphate buffer, pH 7. The deactivation was allowed to proceed for 1 hour, at which point the slides were removed from the solution, rinsed with water and dried.

Microarray Printing: Lyophilized biotinylated goat antibody (goat anti-mouse IgG, biotin-labeled, Pierce) was reconstituted to 1 mg/ml in phosphate buffered saline with 15 mg/ml bovine serum albumin (reconstitution buffer as supplied by Pierce). This stock was then diluted to 100 µg/ml antibody in phosphate buffered saline with varying amounts of Tween20® surfactant. A 384-well source plate was prepared with 20 µl droplets of the antibody solution, with wells dedicated to 0, 0.0001, 0.0005, 0.001, and 0.005, 0.01, 0.05 vol % Tween20®. The coating chemistry was first triple-rinsed with ultrapure (18 MΩ-cm) $H_2O$ and then blown dry with $N_2$ gas prior to arraying. An array of spots was printed on the chemistries using a SpotBot microarrayer (Telechem) fitted with SMP3B pins (Telechem). Spotted slides were incubated at 75% relative humidity for 1.5 hours.

Specific Binding Assay: The specific binding assays were performed at room temperature as follows: chemistries were incubated with 700 µl of 10 µg/ml of Cy3 labeled rabbit anti-goat IgG (Sigma) in PBS (0.1 M sodium phosphate, 0.15 M sodium chloride, pH 7.2), using an adhesive hybridization chamber (described above). Slides were incubated for 30 minutes. The hybridization chamber was then removed and slides were triple-rinsed with PBST (0.1 M sodium phosphate, 0.15 M sodium chloride, pH 7.2, 0.05% Tween20®) then ultrapure (18 MΩ-cm) $H_2O$ and dried. Slide chemistries were placed in a GenePix 4000B scanner (Axon) and settings were optimized for the best signal to noise performance. Final scanner settings were 100% laser power and 460 volt setting on the photo multiplier tube.

Figure 15:
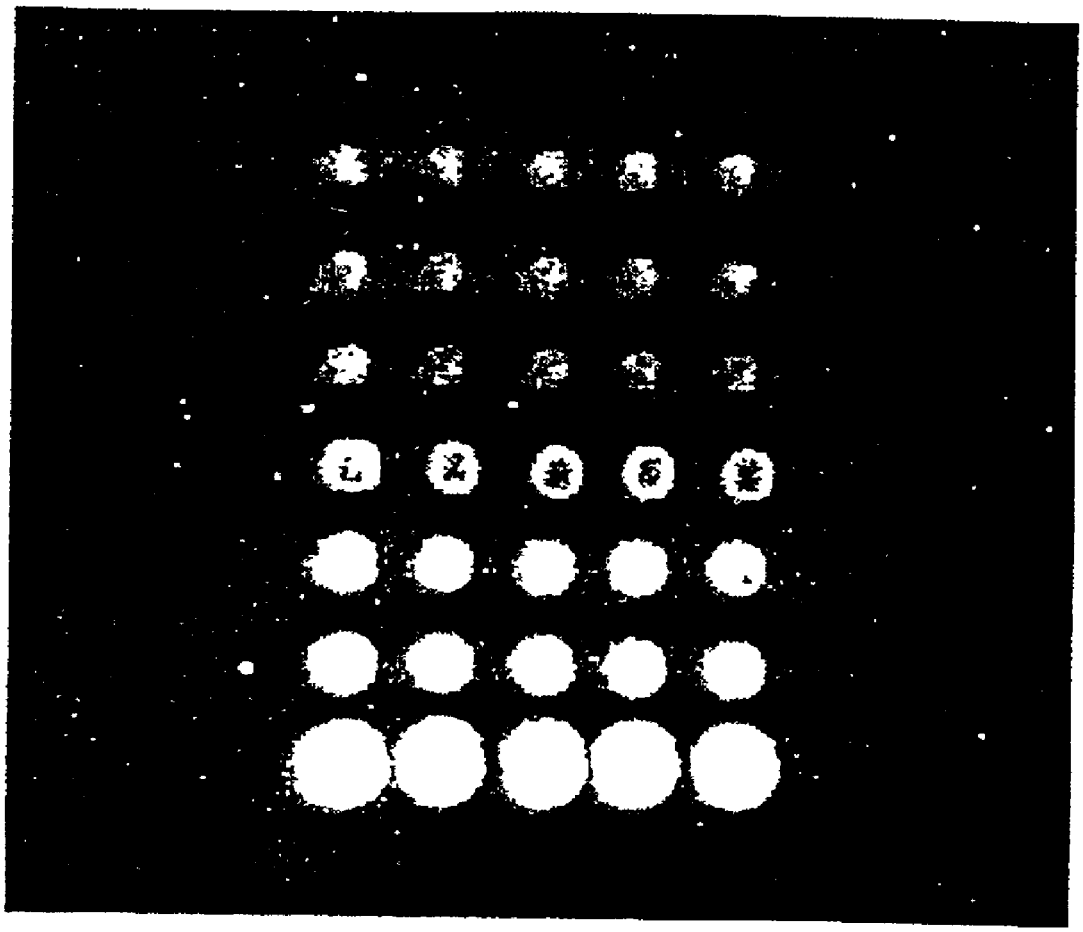
FIG. 15 illustrates the use of one embodiment of the present invention in a protein microarray application, specifically illustrating the use of streptavidin functional surfaces for selective capture of biotinylated antibodies on glass substrate.

Binding Results: A representative array image is presented in FIG. 15. All spots in the image are printed with the same antibody concentration, 100 µg/ml. Each row has a different Tween20® concentration in the buffer, with Tween20® concentration increasing from 0 in the top row to 0.05% in the bottom row. Five duplicate spots are printed in each row. The first observation is that the arrayed antibodies are recognized by the fluorescently labeled detection antibody, demonstrating the surface immobilization of the printed antibody. The addition of Tween20® to the print buffer increases both the size and intensity of the printed spots. Spots in the bottom row have specific binding signal of approximately 9000 relative fluorescence units (RFUs), while the local background is roughly 1000 RFUs.

EXAMPLE XV

Demonstration of Synergistic Effect of Coating Components for Improving Non-Specific Binding Properties of Coated Substrates The following example was designed to show that the combination of components embodied in the present invention provide performance superior to coatings comprised of subsets of these components.

The components in the "standard formula" coating solution can be abbreviated as follows:

| | |
|---|---|
| Biotin-PEG | Biotin-PEG-$CO_2$—N-hydroxysuccinimidyl ester (Shearwater Corp.) |
| Aminosilane | (3-trimethoxysilylpropyl)-diethylenetriamine (Gelest) |
| Azidosilane | 6-azidosulfonylhexyl-triethoxysilane (Gelest) |
| PST | polyoxyethylene sorbitan tetraoleate (Aldrich) |

For this experiment, coating solutions were prepared in the standard formula (as described in Example I), as well as in various subtractions and combinations of these components. In all cases, the volume and ratio of carrier solvents (1:4 DMAC:DMSO) was held constant.

Glass microscope slides were coated as described in Example V.

The surfaces were then assayed for non-specific binding using the procedure described in Example II.

Figure 16:
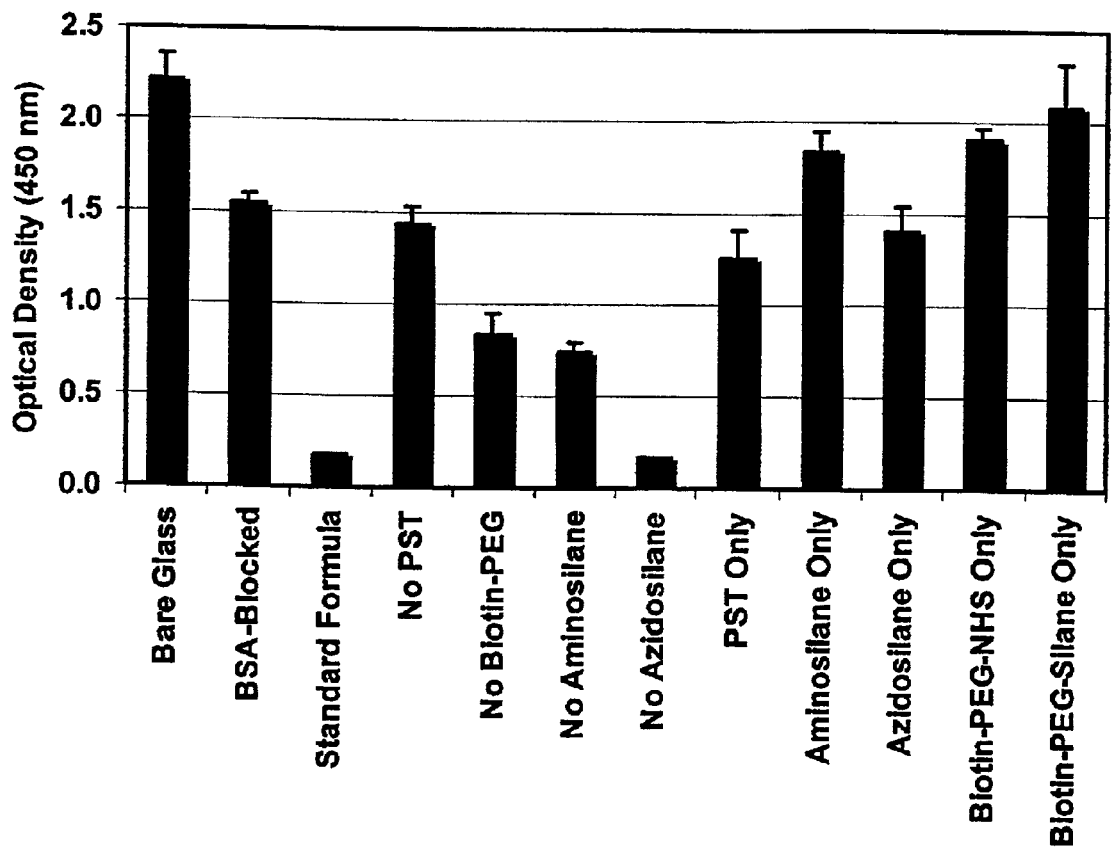
FIG. 16 illustrates the non-specific binding of various coated surfaces demonstrating synergistic effects of the functional surface according to one embodiment of the present invention.

Binding Results: Results are presented in FIG. 16. Results show that the standard formulation provides the best NSB performance relative to all other component combinations, with the exception of the "no azidosilane" formulation, which shows equivalent NSB in this assay. Subsequent experiments have shown that the "no azidosilane" formulation has inferior shelf life relative to the standard formulation. Specifically, once the surface is exposed to water rinse, the low NSB properties of the "no azidosilane" degrade much more rapidly than the standard formulation (days versus weeks or months). This is consistent with the concept that the azidosilane provides some cross-linking/stabilizing role in the surface coating.

The data from this example shows that embodiments of the present invention operate at optimal performance when all the components of the surface coating are present.

EXAMPLE XVI

Demonstration of Additional Matrix Forming Components in the Coating Formulation The following example illustrates the utility of an embodiment of the present invention utilizing alternative matrix-forming molecules, as compared to polyoxyethylene sorbitan tetraoleate (PST). The experiments described here demonstrate other embodiments of the invention, in which alternative matrix-forming molecules provide good non-specific binding and specific binding performance.

Coating solutions were prepared as described in Example II. In addition, coating solutions were also prepared in which the PST was replaced with commercial surfactants, namely Triton X-100 and Tween20. As a control, the matrix-forming component was replaced with glycerol in the formulation. Note that glycerol is not expected to show equivalent matrix-forming ability.

Coating solutions were cast on silicon wafers and cured as described in Example II. The non-specific binding assay was performed as described in Example II. The specific binding assay was performed as described in Example IX.

Figure 17A:
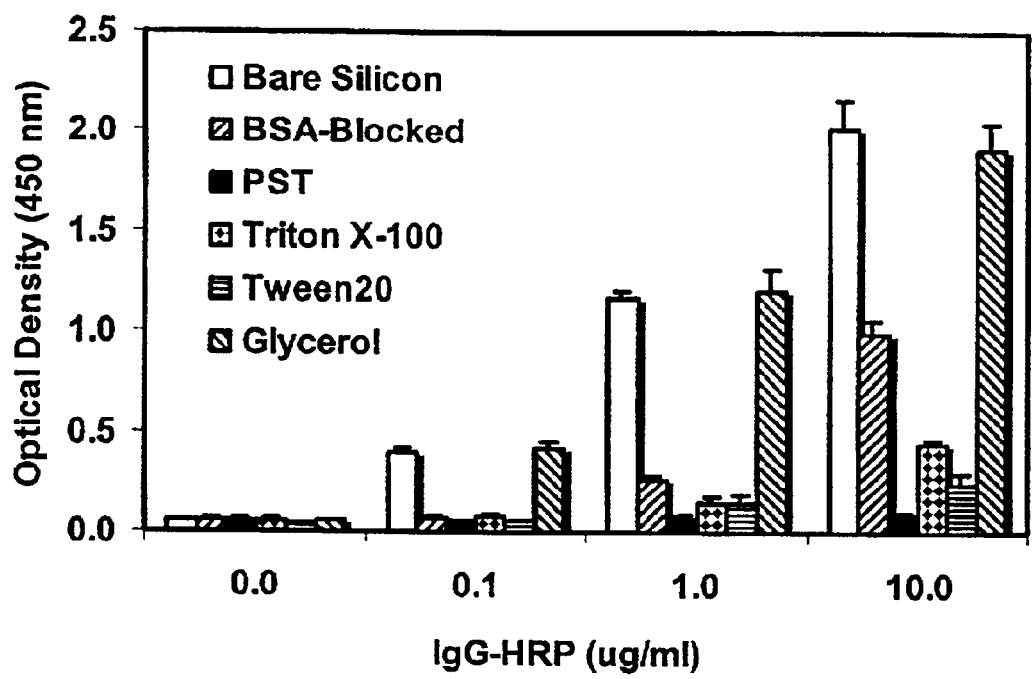
FIGS. 17(a) and (b) illustrates the use of different matrix-forming components in several embodiments of the present invention that show low non-specific protein binding and high specific protein attachment.

Binding Results: Results are presented in FIG. 17. FIG. 17(a) shows that all three matrix-forming components outperform BSA-blocking in the NSB experiment. Of the three tested, the PST gives the best performance, followed by Tween20 and Triton X-100. As expected, coatings made with the glycerol substitute had very high NSB.

Figure 17B:
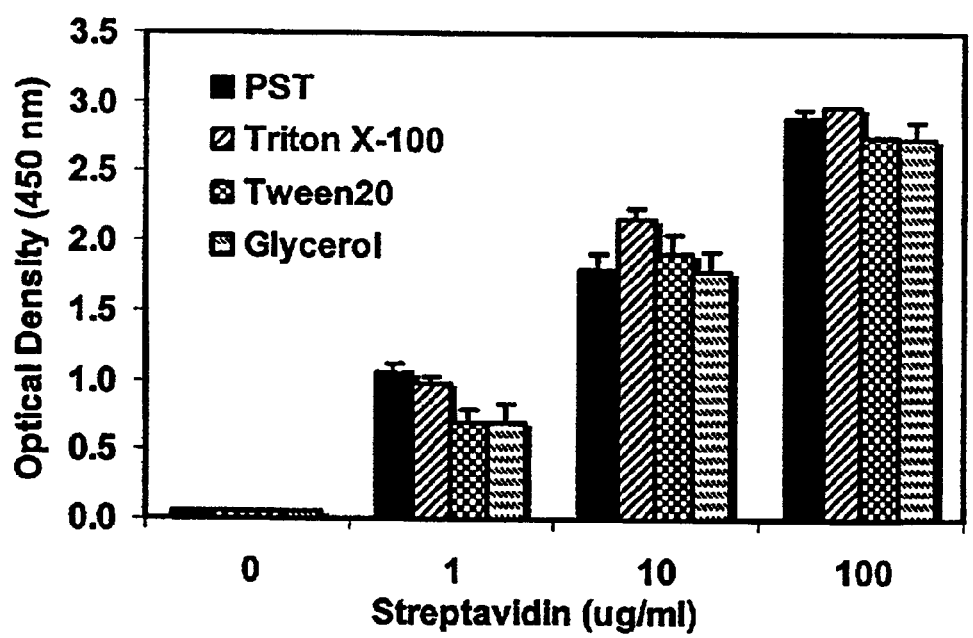

FIG. 17(b) shows that specific binding performance is similar for all three matrix-forming components. Although the glycerol also gives high signal, this is most likely the result of non-specific, rather than specific binding, as suggested by the NSB experiment.

EXAMPLE XVII

Inhibition of Cell Proliferation on Coated Surfaces

The following example illustrates the inhibition of mammalian cell proliferation from culture on one embodiment of the present invention. Coatings were prepared on tissue culture polystyrene substrates in the manner described in Example III.

Cell Culture: Routine cell culture methods using sterile technique and commercial cell culture media and cell lines were employed. Two cell lines were employed (L929 fibroblasts, ATCC, and human umbilical venous endothelial cells, HUVECs, BioWhittaker). Cell culture media for L929 culture, changed every three days, comprised commercial 10% fetal bovine serum in DMEM saline with antibiotic supplements. The control surface was a sterile uncoated tissue culture polystyrene petri dish (BD-Falcon) with cells subject to identical conditions. Cultured stock cells trypsinized from commercial culture ware after reaching confluent phase were plated at a density of $10^5$ per dish and incubated in a commercial cell incubator under 5% $CO_2$ at 37° C.

Figure 18A:
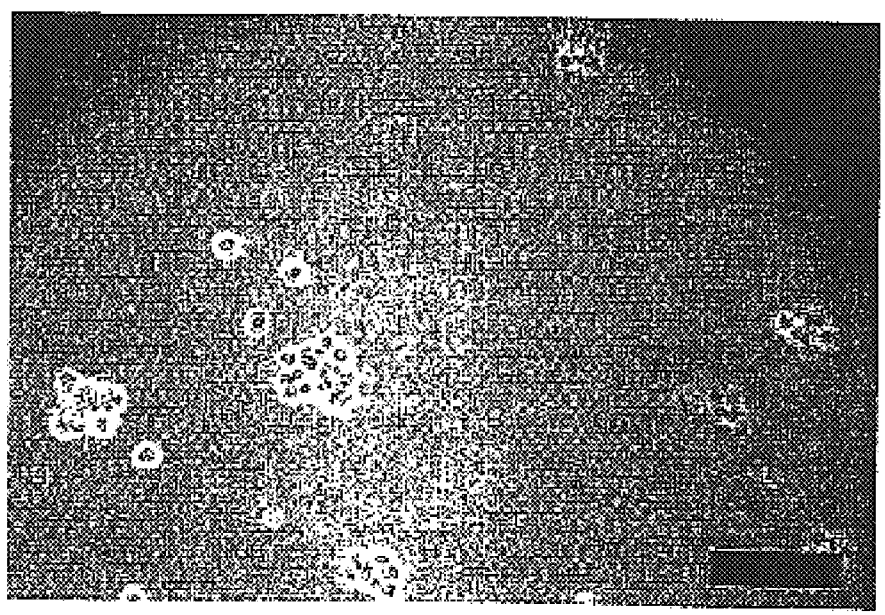
FIGS. 18(a) and (b) illustrates the inhibition of fibroblast cell proliferation after three days of culture on a coated surface embodiment of the present invention (a) relative to a tissue culture polystyrene control (b).
Figure 18B:
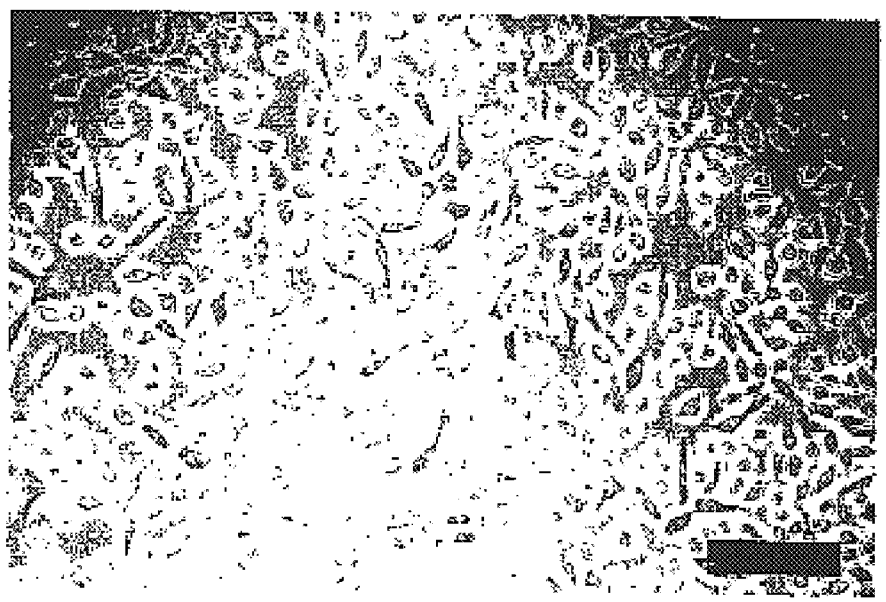

Results: FIG. 18 provides microscope images of the L929 fibroblast cell culture surfaces after three days of growth. The coated surface (FIG. 18(a)) shows few cells relative to the TCPS control (FIG. 18(b)), which shows adherent cell monolayer coverage typical of culture for these cells. The cells that are present on the coated surface appear rounded, in loosely bound clusters, clearly avoiding surface contact and unable to generate confluent cell monolayers or consistent cell attachment. Their rounded shape indicates a stressed condition for these attachment-dependent cells. The control surface shows spread, adherent cells typically observed for these cultures of viable cells. It is believed that the inhibition of extracellular matrix protein adhesion to the coated surface inhibits fibroblast proliferation. Bacterial adhesion and proliferation was also investigated in preliminary experiments. *Pseudomonas aeruginosa* strain PA01 (ATCC, Manassas, Va.) cultured in tryptic soy broth (TSB) per routine microbiological methods to a culture density of ~$10^9$ CFU/ml and inoculated onto coated polystyrene petri dishes in various dilutions from this stock using TSB. Bacteriological grade polystyrene (BD) was used a control surface. After 24-hour incubation in a culture incubator (37° C.) and rinsing with TSB, few adherent microbes were observed on the coated surface using phase contrast microscopy (40× magnification). By contrast, the control surface was colonized with adherent viable organisms to high density, not removable by media rinsing (data not shown).

It will be clear that the invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed herein and as defined in the appended claims.

All publications cited herein are hereby incorporated by reference.

What is claimed is:

1. A method of preparing a functional surface, said method comprising:

providing a substrate;

providing an effective amount of active component comprising a functional group, spacer group, and a binding group;

providing an effective amount of cross-linking component;

providing an effective amount of matrix-forming component;

affixing said active component, said cross-linking component and said matrix forming component onto said substrate, thereby forming a functional surface.

2. The method of claim 1, wherein said affixing further comprises coating said active component, said cross-linking component and said matrix forming component onto said substrate creating a coated substrate and curing said coated substrate.

3. The method of claim 2, wherein said curing is thermal activation.

4. The method of claim 1, wherein said functional group is biotin.

5. The method of claim 1, wherein said spacer group is polyethylene glycol.

6. The method of claim 1, wherein said binding group is a silanes.

7. The method of claim 1, wherein said binding group is an alkoxysilane.

8. The method of claim 1, wherein said cross-linking component is acrylates.

9. The method of claim 1, wherein said matrix-forming component is a polyoxyethylene-based surface-active substances.

10. The method of claim 1, wherein said matrix-forming component is polyoxyethylene sorbitan tetraoleate.

* * * * *